(12) United States Patent
Scott

(10) Patent No.: US 7,599,803 B2
(45) Date of Patent: Oct. 6, 2009

(54) HYDROCARBON WELL TEST METHOD AND SYSTEM

(75) Inventor: Bentley N. Scott, Garland, TX (US)

(73) Assignee: Phase Dynamics, Inc., Richardson, TX (US)

( * ) Notice: Subject to any disclaimer, the term of this patent is extended or adjusted under 35 U.S.C. 154(b) by 137 days.

(21) Appl. No.: 11/499,391

(22) Filed: Aug. 4, 2006

(65) Prior Publication Data

US 2007/0239402 A1    Oct. 11, 2007

Related U.S. Application Data

(60) Provisional application No. 60/789,323, filed on Apr. 5, 2006.

(51) Int. Cl.
G06F 19/00    (2006.01)
(52) U.S. Cl. ........................................ 702/24
(58) Field of Classification Search .................... 702/24
See application file for complete search history.

(56) References Cited

U.S. PATENT DOCUMENTS

| | | | |
|---|---|---|---|
| 4,864,127 A * | 9/1989 | Brame ........................ 250/253 |
| 5,259,239 A | 11/1993 | Gaisford | |
| 5,260,667 A | 11/1993 | Garcia-Golding | |
| 5,576,974 A | 11/1996 | Marrelli et al. | |
| 5,654,502 A | 8/1997 | Dutton | |
| 5,926,024 A * | 7/1999 | Blount et al. ................ 324/324 |
| 6,234,030 B1 | 5/2001 | Butler | |
| 6,318,156 B1 | 11/2001 | Dutton et al. | |
| 6,327,914 B1 | 12/2001 | Dutton | |
| 2005/0081643 A1 | 4/2005 | Mattar et al. | |
| 2005/0279131 A1 * | 12/2005 | Battiste et al. ................. 62/611 |
| 2006/0141637 A1 * | 6/2006 | Hassell ........................ 436/180 |

* cited by examiner

Primary Examiner—Tung S Lau

(57) ABSTRACT

Methods and systems for testing a hydrocarbon well. Real time monitoring of the flow stream discharging from a well is used to collect physical and electromagnetic characterization data on the flow stream. A data filter is used to exclude data points uncharacteristic of the true performance of the well at that time in the operational cycle of the well. A statistical evaluation during or after at least some data has been collected is used to determine when the data set meets an acceptable level of data quality. The filtering parameters are adjusted to improve future detection, correction, and filtering of uncharacteristic data. Corrective transforms can be derived and applied to selected uncharacteristic data to recondition and retain the data. The filtered and completed data set is used to generate a hindsight determination of crude petroleum oil production output, including petroleum oil, water, and gas fractions and production rates.

14 Claims, 13 Drawing Sheets

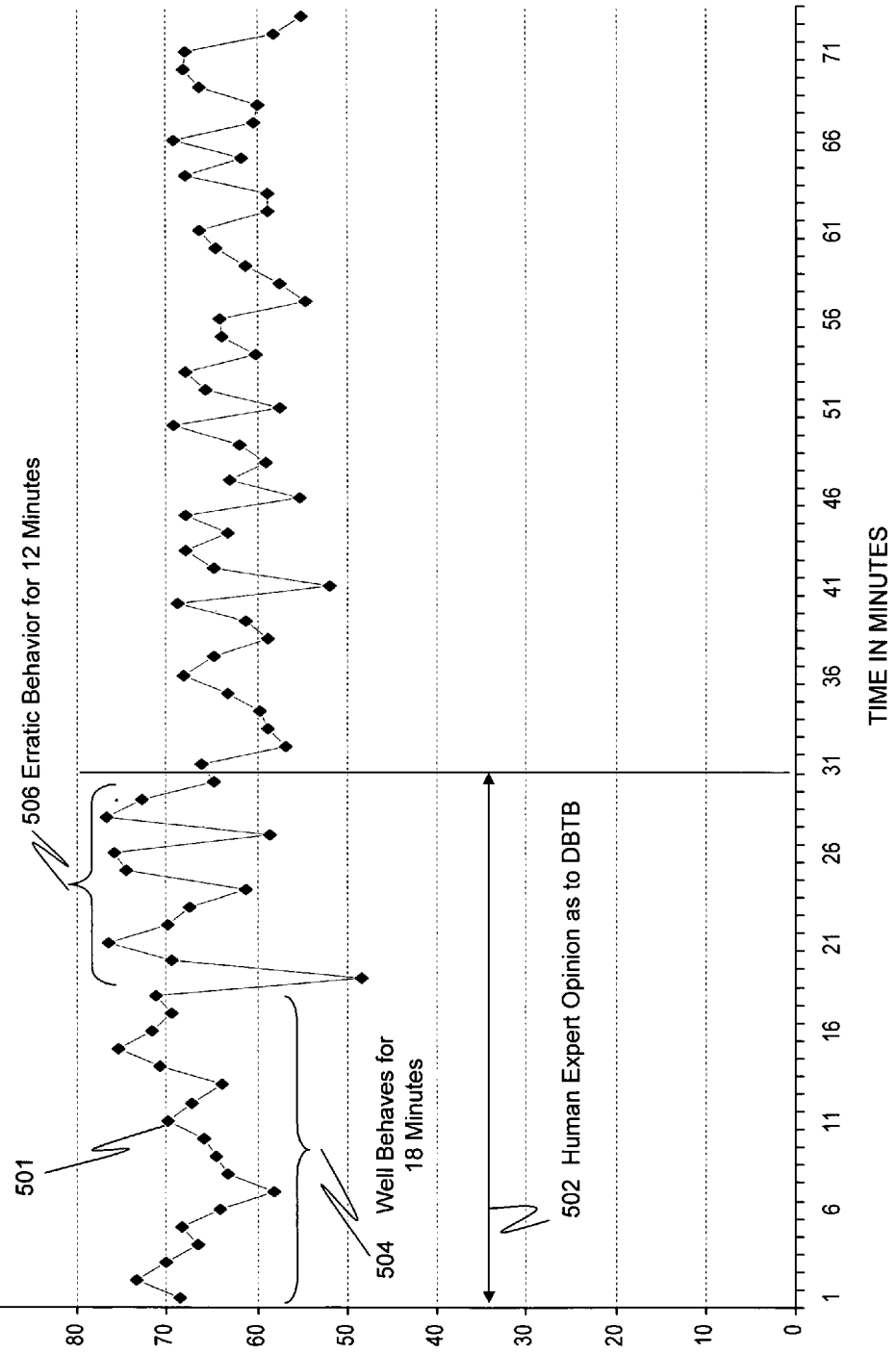

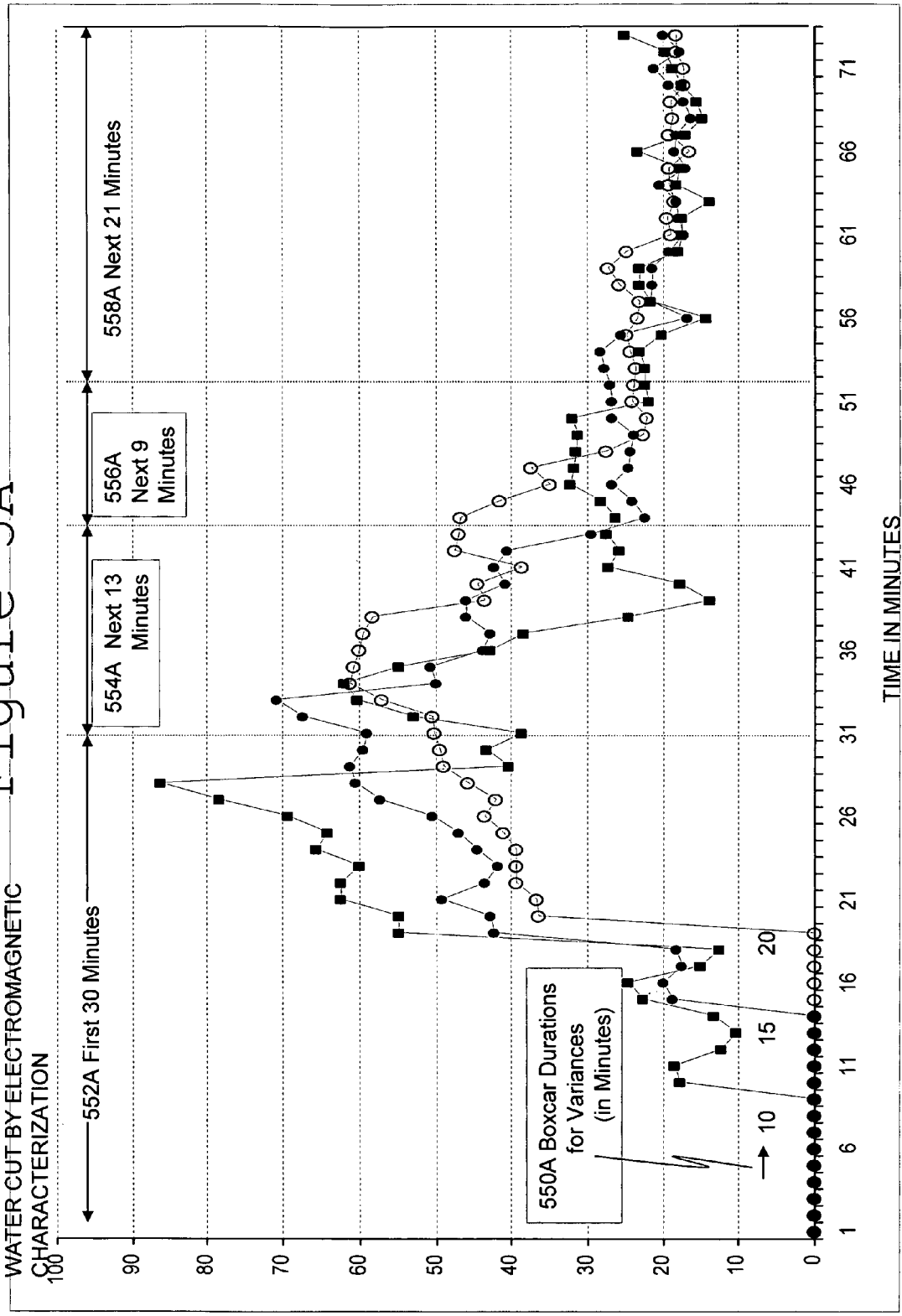

Figure 5C

Average Value of Maximum Variance = 32 minutes
For the 10, 15, and 20 Minute Boxcars ATDBTB = Adaptive Time Delay Before Test Begins for this example is thus 32 minutes.

| Period | Minutes Long | Average % WC | Average Variance of All 3 BoxCars |
|---|---|---|---|
| 552A | 30 | 67.946 | 42.159 |
| 554A | 13 | 62.397 | 45.962 |
| 556A | 9 | 62.532 | 28.314 |
| 558A | 21 | 62.525 | 19.608 |
| 1A | First 32 | 67.536 | 43.370 |
| 1B | Last 41 | 62.541 | 28.424 |

Difference Calculation: Period 558A, Period 1B = 0.016%
Difference Calculation: Period 554A, Period 1B = 0.104%

Reproducibility for the Distillation Analytical Method for % WC per ASTM d4006 = 0.110 %
Reproducibility for the Titration Analytical Method for % WC per ASTM D4337 = 0.100 %

HYDROCARBON WELL TEST METHOD AND SYSTEM

CROSS-REFERENCE TO RELATED APPLICATIONS

This application claims priority from U.S. Provisional Patent Application 60/789,323 filed on Apr. 5, 2006, which is hereby incorporated by reference.

BACKGROUND AND SUMMARY OF THE INVENTION

The present application generally relates to methods and systems for measuring the amount of petroleum, gas, and water produced from a hydrocarbon well.

The following paragraphs contain some discussion, which is illuminated by the innovations disclosed in this application, and any discussion of actual or proposed or possible approaches in these paragraphs does not imply that those approaches are prior art.

Background: Production of Crude Petroleum Oil

Crude petroleum oil and gaseous hydrocarbons are produced by extracting them from subterranean reservoirs. Sometimes the oil and gas flows to the surface due to the natural pressure when a well is first drilled. Often, however, other methods are required to bring them, and particularly the oil, to the surface. These include a variety of pumping, injection, and lifting techniques used at various locations, such as at the surface wellhead (e.g. use of rocking beam suction pumping), at the bottom down-hole of the well (e.g. use of submersed pumping), all along with well casing string (e.g. use of gas injection lifting), and in the subterranean oil formation reservoir surrounding the well (e.g. water, combustion, or steam-driving the reservoir or formation). Each of these techniques results in crude petroleum oil and gas emerging from the well head as a multiphase fluid of varying proportions of oil, water, and gas. For example, a gas lift well has large volumes of gas associated with the well, with gas-to-oil volumetric ratios as high as 200 standard cubic feet of gas per barrel of oil, or higher. As another example, a water-drive reservoir can produce oil as an oil and water mixture, with water content percentages as high as 99%. In the petroleum industry, the water fraction in oil is known as the water cut ("WC") and the oil fraction is referred to as the oil cut ("OC").

Hydrocarbon well optimization methods include adjusting the well operating parameters and employing reservoir stimulation techniques. Decisions in the use of such optimization methods are greatly enhanced if accurate compositional data of the oil is available, both instantaneously and over time. Specifically, in one context of hydrocarbon well production optimization, it is important to be able to determine the amount of water mixed with the crude oil, which is often present as naturally-produced ground water, water from steam injection, and/or well injection water which has become eventually mixed with the oil as a result of a reservoir stimulation process. One such stimulation process is known as Steam Assisted Gravity Drain stimulation ("SAGD"). Another is the "Huff and Puff" stimulation method where steam is intermittently injected into the reservoir. Different types of stimulation processes can have different phase states upon start-up of the well.

As a further complexity to the multiphase characteristics of crude petroleum oil, a given well with a given production technique does not produce a constant multiphase composition and flow rate. First, wells deplete hydrocarbon-bearing reservoirs and/or formations, and there is generally, a decreasing output of hydrocarbon over days, weeks, months, or years of time. On the other hand, well composition and volumetric output can change in a matter of seconds. For example, upon start-up, a well can take several minutes or several hours to reach steady-state operation. Pressure, temperature, composition, and flow rate swings can occur during start-up. Second, some wells are in a constant state of composition and flow rate change. For example, one production technique uses intermittent gas injection lifting. Gas is periodically injected into the well purposefully, resulting in a periodic cycle to the well output, as in a waveform.

One constant requirement for all hydrocarbon well operations, regardless of production technique, is the need to determine how much oil and gas a given well is producing over a given period, e.g. the well production rate. To that end, well testing is routinely conducted on a given well to establish the composition and flow rate.

The variable production techniques and the resulting varying multiphase fluids present significant challenges to well testing systems and methods. For the most part, determination of the total volume of gas and volume of liquid produced over a given time is relatively easily established using gas-liquid separation techniques, and gas and liquid flow metering techniques known to a person having ordinary skill in the art of quantifying hydrocarbon well output production. However, a significant challenge lies in determining how much water is mixed with the petroleum oil in the total liquid output. Further, water cut can vary significantly, depending on a number of factors, including natural sources of underground water, well startup conditions, well upsets, and the production technique.

The need for accurately characterizing a particular well's performance is important to well operation and production output optimization. Optimization operations include reducing equipment failure and improving decisions to work-over the well. Reasons causing variable multiphase flows include drill string behavior, various bottom whole configurations to access more than one hydrocarbon formation at a time, and possible differing layers of oil and gas in a given hydrocarbon formation. Issues in interpreting the well characterization data include differing patterns of well behavior, various cyclic well behaviors, and varying durations of peak and minimum flows.

Background: Water Cut Analyses in Oil Production

When water is pumped to the surface of the Earth along with the crude petroleum oil, producers often attempt to physically separate the water from the oil, because the water can corrode pipes and damage down-stream processing equipment. Producers attempt to optimize the oil and gas production but minimize the water production. Further, the water has no value relative to the oil and in-fact can become a disposal or environmental problem wherever it is finally removed. Water-oil "separators" or liquid-liquid decanters are thus often used, before the crude petroleum oil is further transported from a well site or tank farm. However, the efficiency of such separators in achieving two pure streams of oil and water is often not 100%, and free water is still frequently entrained in the crude petroleum oil as it enters storage, in the range of about 0.10% to about 5%.

The need for a very accurate determination of water content and validation of the amount of water in crude petroleum oil is particularly important during the taxation of crude petroleum oil and the sale of crude petroleum oil, where the owner or seller of the oil does not want to pay taxes on water and the customer does not want to pay the price of oil for water. To that end, multiple determinations and cross-checks are often conducted on-line and off-line during petroleum production.

The offline method involves physically sampling the stream and analyzing it in a laboratory setting. In the petroleum industry, the sampling is usually done using a composite sampler which automatically opens a sample valve attached to a pipeline at some frequency to collect an aggregate sample into a sample container. The objective is to collect a sample which is representative of the production period of petroleum under consideration. After collection, the composite sample is usually picked up by a person and taken to a laboratory. The composite sample is then "sampled" to prepare aliquots, or sub-divisions of the composite sample, for each of the various characterizations, or analysis methods, to be used.

Three off-line analytical methods are commonly used for determining the water content of crude petroleum oil. These are the centrifuge method, the distillation method, and the titration method. See the American Petroleum Institute ("API") Manual of Petroleum Measurement Standards, Chapter 10. The distillation and titration methods are relatively accurate, but are plagued by long analysis times and not suitable for use in the field or at the point of sale. The centrifuge method is quicker, but almost always under-reports the amount of water present. The American Society for Testing of Materials has reported the standard analytical errors for water content measurements using the three methods. The repeatability errors are 0.11% for the distillation method (see ASTM D4006), 0.15% for the titration method (see ASTM D4377), and 0.28% for the centrifuge method (see ASTM D4007). Note that the API does not have standardized methods for testing crude petroleum oil with water cuts above 2%.

Note that composite petroleum samplers and the associated analytical methods have other kinds of problems and disadvantages other than, for example, meeting a desired accuracy for a given determination. For example, results for composite samplers are typically only available at the end of a batch or a test, and there is no recourse if something goes wrong with the sampling system during the sampling process. At the end of the sampling and analysis, only a single number is available to consider. Additionally, the exposure of personnel to hazardous liquids associated with processing the samples is undesirable. Thus, the petroleum industry has continued to seek other methods that provide the required accuracy, speed, and safety.

One other standard on-line method is the use of two way or three way test separator vessels. This approach generally uses a tank sized to attempt to separate the well output into two or three streams, such as a gas stream, a water stream, and an oil stream, and then separately meter each stream. The Petroleum Engineering Handbook, $3^{rd}$ Printing, from the Society of Petroleum Engineers, Richardson, Tex., Howard B. Bradley editor-in-chief, 1992, is hereby incorporated by reference. It describes such separators in Chapter 12. However, this approach has several drawbacks including susceptibility to not being able to separate emulsions of oil and water, large holdup volume, and large physical footprint.

Accordingly, the use of rapid on-line instruments such as densitometers, capacitance probes, radio frequency probes, and microwave analyzers to measure water content of petroleum products is becoming more common. In addition to providing increasingly accurate determinations of water content, real time water content results via on-line methods can provide beneficial operational advantages. Knowledge of when water becomes present in petroleum as it is being produced and the magnitude of the quantity of the water may provide an opportunity to divert the water before it reaches a transport pipeline, storage vessel, or shipping tanker. Additionally, the real time data may show if the water is detected in several short periods of time or if it is present across the entire production period. Furthermore, real time analyzer results can be compared to composite sampler results. Finally, on-line measurements of properties via unmanned instrumentation reduces the need human involvement in the process of measuring the composition of crude petroleum oil.

Background: Water Cut by the Density and Electromagnetic Characterization Methods On-line densitometers can be used to ascertain the amount of water in petroleum oil. One on-line density method uses a Coriolis meter. This meter can be installed in the pipeline leaving the well or wells. Coriolis meters measure the density of a fluid or fluid mixture, and usually its mass flow rate as well, using the Coriolis effect. Then, calculations can be performed to indirectly determine the water percentage. For example, a Coriolis meter can measure the density of a water-oil mixture, $\rho_{mixture}$, and then perform a simple calculation method to determine the individual fractions or percentages of the water phase and oil phase. By knowing or assuming the density of the dry oil, $\rho_{dry\ oil}$, and the density of the water phase, $\rho_{water\ phase}$, then a water weight percentage, $\psi_{water}$, can be calculated as follows:

$$\psi_{water\ phase} = ((\rho_{mixture} - \rho_{dry\ oil})/(\rho_{water\ phase} - \rho_{dry\ oil})) \times 100$$

Note that the above equation can work equally well using the specific gravities of the mixture, dry oil, and water phase, where specific gravity is the ratio of the particular density to the density of water at 4 degrees Celsius.

It should be recognized that the water percentage by density method is subject to uncertainty. First, due to natural variations of, for example, the hydrocarbon composition of crude petroleum oil, the density of the dry oil can vary significantly from the assumed or inputted value required for the simple calculation. Such a value inputted into a densitometer based on a guess or on history of a given oil well. Crude petroleum oils can range from about 800 kilograms per cubic meter ($kg/m^3$) to about 960 $kg/m^3$. Further, the water encountered in oil well production is most often saline. This salinity is subject to variability, ranging from about 0.1% by weight salt to about 28%. This results in a variation in the density of the water phase from about 1020 $kg/m^3$ to about 1200 $kg/m^3$. Again, this value would be inputted into a densitometer based on a guess or on the history of a given well.

Note also that an entrained gas phase, as is sometimes present, can dramatically affect the density of a crude petroleum oil liquid stream as measured by a Coriolis meter, if a precise correction method is not applied for the presence of the gas.

Another technique to determine the water percentage is to use a microwave analyzer, instead of a densitometer, to perform the in-line monitoring of the oil and water mixture.

U.S. Pat. No. 4,862,060 to Scott (the '060 patent), entitled Microwave Apparatus for Measuring Fluid Mixtures and which is hereby incorporated by reference, discloses microwave apparatuses and methods which are most suitable for monitoring water percentages when the water is dispersed in a continuous oil phase.

Note that the change in fluid mixture dielectric properties for a water and oil mixture can be affected by a number of parameters, including not only the percentage of water in oil, but also the individual dielectric constants of the oil phase and the water phase. For example, the dielectric constant of the dry crude petroleum oil itself can vary depending on its density and chemical composition. Note that temperature can affect the density of the oil and the water and thus the dielectric properties of each component and the mixture. However, temperature variations can easily be compensated for by using a temperature probe in-contact with the multiphase fluid being characterized to allow referencing to data sets or curves fit to the data sets for different temperatures.

Thus, both the densitometer method ("water cut by density") and the electromagnetic characterization method ("water cut by electromagnetic characterization") are subject to uncertainties. One approach to dealing with the uncertainty is to simultaneously use both methods to characterize a crude petroleum oil stream for water content. This joint use is practiced commercially. An example is the Compact Cyclone Multiphase Meter manufactured by Phase Dynamics, Inc. of Richardson, Tex.

When conducting joint densitometry and electromagnetic characterizations of a flow stream of mixtures of water and crude or partially refined petroleum oils, exact values of the electrical and physical properties of the pure water and oil phases are not always known. However, in certain situations, each method can supply estimates of the requires values to assist each other in determining water content in petroleum products.

An example of a such a supply of a physical property estimate is disclosed in U.S. patent application Ser. No. 11/273,613 to Bentley N. Scott entitled Methods for Correcting On-Line Analyzer Measurements of Water Content in Petroleum, and is hereby incorporated by reference, and hereinafter referred to as Scott '3613. Scott '3613 discloses that because a microwave analyzer is usually shop-calibrated across a range of water contents using a dry oil of a known density, the analyzer will report an erroneous water percentage if the dry oil being measured in the field shifts to a different density than that of the original dry calibration oil. The auto-correction method disclosed in Scott '3613 ameliorates this problem. Scott '3613 teaches that there is 0.03% WC by electromagnetic characterization error introduced for every 1 $kg/m^3$ shift in actual dry oil density from the dry oil calibration density. It discloses that for water cut's less than about 5%, the density of the actual dry oil can be adequately estimated for use in calculations by the microwave analyzer by assuming the actual dry oil density is equal to the density of the mixture as measured by the densitometer. This assumption results in a maximum error rate of about 0.23% at about 5% water cut. This error rate compares favorably to the off-line analytical method error rates previously detailed. For well testing the error is more difficult to define and must be done by statistical methods of pulling a population of samples large enough to find a statistical mean and standard deviation. This method is not well defined and the true error is not known since each sample is an independent one and is subject to many errors with equipment and personnel. Since the lab method does not have a known standard error the resulting data is a measure of the reproducibility of the on line analytical equipment and the laboratory methods and handling of the samples.

Background: Crude Petroleum Oil Phase Behavior and Electromagnetic Characterizations Still further uncertainty in conducting characterizations of crude petroleum oil can be caused by the physical chemistry of the oil, the water, and the mixture itself. For example, in the case of liquid-liquid mixtures undergoing mechanical energy input, the mixture usually contains a dispersed phase and a continuous phase. For water and oil, the mixture exists as either a water-in-oil or an oil-in-water dispersion. When such a dispersion changes from water phase continuous to oil phase continuous, or vice-versa, it is said to "invert the emulsion phase". This is a rheological phenomenon.

Dispersion of one phase into another occurs under mechanical energy input such as agitation, shaking, shearing, or mixing. When the mechanical energy is reduced or eliminated, coalescing of the dispersed phase can occur, where droplets aggregate into larger and larger volumes. Further, in a substantially static situation (e.g. reduced energy input), heavy phase "settling-out" or stratification can occur under the force of gravity.

A further complicating phase-state phenomena of liquid-liquid mixtures is that stable or semi-stable suspensions of dispersed-phase droplets can sometimes occur. This is usually referred to as an emulsion, which can be either stable or semi-stable. Certain substances are known as emulsifiers and can increase the stability of an emulsion, meaning that it takes a longer time for the emulsion to separate into two phases under the force of gravity or using other means. In the case of petroleum oils, emulsifiers are naturally present in the crude petroleum oil. For example, very stable emulsions can occur during petroleum processing, as either mixtures of water-in-oil or oil-in-water.

Another complicating phenomena is that the formation of dispersions and emulsions are sometimes "path-dependent." Generally, path-dependence exists when the result of a process depends on its past history, i.e. on the entire sequence of operations that preceded a particular point in time, and not just on the current instantaneous conditions. In the case of emulsions, the process of forming the emulsion can be path dependent because the sequence of phase addition, mixing, and energy inputs can affect which phase becomes the dispersed phase and how stable the resulting emulsion is. Thus, if one does not know the history of the multiphase fluid undergoing dispersion or emulsification, one will not always be able to predict the "state" of the dispersion or emulsion, i.e. which phase is continuous and which is dispersed, even if the proportions of the phases are accurately known at a particular point in time.

For microwave analyzers, whether a dispersion or emulsion is water-continuous or oil-continuous has a significant effect on the analyzer's measurements. In the case of water-continuous dispersions or emulsions, the conductivity path established by the water continuous phase causes a significant change in the measured permittivity relative to the same proportion of phases existing as an oil continuous dispersion or emulsion. Additionally, further variations in the conductivity of the aqueous or water continuous phase caused, for example, by even relatively small changes in salinity, can significantly affect the measured permittivity results. Note that when the non-aqueous or oil phase is continuous, no conductivity path is established (because the droplets are not "connected" to form a continuous conducting circuit) and hence there is no significant effect on the measurements of a microwave analyzer due to the conductivity of the aqueous phase. Note also that this is only true when the wavelength of the electromagnetic energy is large compared to the emulsion size. When the emulsion size is larger than one eighth of a wavelength the voltage difference across the emulsion can be significant and therefore a correction must be made with respect to the salinity (conductivity at the frequency of measurement) of the water.

As a particular example of the complex behavior of oil-water mixtures and the impact of that behavior on electrical characterizations such as permittivity, consider FIG. 1A. It is a generalized phase diagram 100 of a particular crude petroleum oil and a range of aqueous solutions of varying salinity where the fraction of the water phase, $X_w$, is plotted against the frequency, f, as instantaneously read by a microwave analyzer. Note that although the lines are shown as straight lines the relationship between $X_w$ and f may not be strictly linear. To illustrate aspects of the complex behavior of liquid-liquid mixtures, consider starting with a pure oil phase that is under-going a given amount of mechanical energy input, as is encountered when such a fluid is pumped through a restricting valve and is experiencing a pressure drop. This starting composition, on the path independent, oil-continuous line 101, is represented by point 102. Then, an aqueous saline solution could be added to the oil phase to form a mixture of water-in-oil, represented by points on line 101. The relationship between the permittivity frequency and the aqueous phase fraction is determined by the line 101. On this line, the multiphase fluid exists as an oil continuous phase with drops of dispersed aqueous phase. Then, increasing amounts of saline solution can continue to be added, up along line 101 to point 104. At point 104, the dispersion progresses along path dependent line 105 to point 106. At point 106, the dispersion inverts to an aqueous phase continuous dispersion, with an accompanying discontinuity in measured permittivity, jumping to a particular permittivity curve depending to a large extent on the salinity of the aqueous phase. Aqueous phase can continue to be added along salinity iso-lines in zone 107 to path-independency transition level 108. At path-independency transition level 108, path dependency is no longer present as the dispersion moves into zone 109. The fraction of aqueous phase can be increased to 1.00, with the permittivity being dependent on both the salinity and the fraction of the aqueous phase.

It should be noted that in certain emulsions, zone 107 may not exist at all, and line 105 might transition directly to zone 109.

In an another example of possible path dependency, the mixture may begin as a point located some where in a high water cut, path independent, salinity-controlling, aqueous continuous zone 109. Then, the aqueous fraction could be reduced to path-dependency transition level 110, and further reduced to aqueous fraction 112, along the iso-salinity lines within the high water cut, path dependent, aqueous-continuous zone 111. The iso-salinity lines within zone 111 are shown as dashed lines because they represent salinity levels which may be the same as that in zone 107. Additionally, path-dependency transition level 110 may or may not be equal to path-independency transition level 108.

Next, following the iso-salinity lines through zone 107, the dispersion would invert at aqueous fraction 112, and as aqueous fraction is further reduced, the relationship follows oil-continuous, path-dependent line 113 to point 104.

It should be noted that in certain emulsions or dispersions, zone 111 may not exist at all, and line 113 might transition directly from zone 109.

Thus, for the particular crude petroleum oil example above as it is mixed in various proportions with a variable salinity aqueous phase, at least three zones of compositional uncertainty can exist for the permittivity of aqueous continuous dispersions, of which at least two such zones are path-dependent. Additionally, at least three discrete curves can further relate the permittivity of oil-continuous mixtures, of which at least two such curves are path dependent.

Such complex physical chemistry leads to numerous uncertainties with regards to electromagnetic-energy-based composition determinations. For example, referring again to FIG. 1A of this application, frequency 114 can in-fact represent two different mixture compositions, 116 and 118, depending on how such compositions were formed, as previously described. Additionally, a particular aqueous fraction 119 can correspond to either an aqueous phase dispersion of varying salinity contents, points 120, each having a corresponding permittivity frequency (not shown) or an oil-continuous phase dispersion of a particular frequency 122.

It has been found that these compositional and permittivity frequency uncertainties can be reduced by using a number of methods, depending somewhat on which zone or curve the mixture state resides in or on. For example, to address the problems of phase inversion uncertainties in aqueous and non-aqueous multiphase mixtures, U.S. Pat. No. 4,996,490 to Scott (the '490 patent), entitled Microwave Apparatus and Method for Measuring Fluid Mixtures and which is hereby incorporated by reference, discloses microwave apparatuses and methods for accommodating phase inversion events. For the example of oil and water mixtures, the '490 patent discloses that whether a particular mixture exists as an oil-in-water or a water-in-oil dispersion can be determined by differences in the reflected microwave power curves in the two different states of the same mixture. Therefore, the '490 patent disclose microwave apparatuses and methods, including the ability to measure microwave radiation power loss and reflection to detect the state of the dispersion. In further embodiments of that invention, methods are disclosed to compare the measured reflections and losses to reference reflections and losses to determine the state of the mixture as either water-in-oil or oil-in-water, which then allows the proper selection and comparison of reference values relating the measured microwave oscillator frequency to the percent-age water. An embodiment of the '490 patent is reproduced from that patent in FIG. 1B, which explained and described in detail later in this Application.

Thus, referring again to FIG. 1A of this application, for water fraction 119, the apparatus and the method of the '490 patent would be able to identify whether the dispersion is in zone 111 or on line 105. When the composition is on line 105, microwave analyzers using the method of the '490 patent are able to accurately determine the aqueous phase fraction.

Thus, solving the problem of accurately ascertaining the composition of crude petroleum presents challenges and requires solutions not adequately met by current approaches. More particularly, there is an increasing need for reduction of uncertainty in the characterization of crude oil as the value of petroleum continues to rise. More specifically, as the use and development of different production enhancement techniques continues to increase, the dynamics of compositional fluctuations at the wellhead adds further challenges to accurately determining crude petroleum oil production output.

Hydrocarbon Well Test Systems and Methods

The present application discloses systems and methods for characterizing a multiphase flow stream produced from a hydrocarbon well. As live characterization data is collected from a well discharge flow stream, a time series of measurements results. The systems and methods of the present application can filter the time series of data and then can assess the filtered time series for acceptable data quality. If the quality is acceptable, at least one characterization measurement can be outputted and filtering parameters can be selectively adjusted. If the quality is not acceptable, more data can be collected and the method can eb repeated until acceptable quality is achieved.

In some embodiments (but not necessarily all), the disclosed innovations can be used at the wellhead of (or slightly downstream from) a producing hydrocarbon well, to estimate the oil, water, and gas output.

In some embodiments (but not necessarily all), the disclosed innovations can be used at the wellhead of (or slightly downstream from) a producing hydrocarbon well and can use time series of measurements which include an electromagnetic characterization property, such as microwave permittivity, and a physical property, such as fluid density.

In some embodiments (but not necessarily all), the disclosed innovations can be used at the wellhead of (or slightly downstream from) a producing hydrocarbon well to improve the characterization of that well upon re-testing or start-up of that well.

The disclosed innovations, in various embodiments, provide one or more of at least the following advantages:

Some of the disclosed innovations can provide methods and systems to improve the characterization of hydrocarbon well production output using a single characterization system with improved accuracy across a wide variety of operating conditions.

Some of the disclosed innovations can provide methods and systems to reduce uncertainty caused by non-steady state gas or liquid phase behavior for a particular hydrocarbon well.

Some of the disclosed innovations can provide methods and systems to reduce the uncertainty caused by changing physical and electromagnetic properties of the aqueous, oil, and gas phases discharging from a particular hydrocarbon well and/or reservoir.

Some of the disclosed innovations can provide methods and systems to reduce the uncertainty caused by faults and/or spurious results and/or errors in the operation of a multiphase electromagnetic characterization system.

Some of the disclosed innovations can provide more accurate physical and/or electromagnetic property measurements.

Some of the disclosed innovations can provide near-real-time reduction of uncertainty to improve near-real-time manned or unmanned well-operations decision-making, such as whether to review a particular well's performance.

Some of the disclosed innovations can provide near-real-time reduction of uncertainty to improve the accounting of oil, water, and gas production from a particular hydrocarbon well.

BRIEF DESCRIPTION OF THE DRAWINGS

The disclosed inventions will be described with reference to the accompanying drawings, which show illustrative, non-limiting embodiments of the invention and which are incorporated in the specification hereof by reference, wherein:

FIG. 5 shows an example of the minute-by-minute time series of water cut of an actual hydrocarbon well after having been switched into test service, consistent with a preferred embodiment.

FIG. 5A shows the minute-by-minute time series of the statistical variance of water cut, calculated with different boxcar durations for the variance period, from the same well test example as in FIG. 5, consistent with a preferred embodiment.

FIG. 5C shows a table of statistical results from FIGS. 5, 5A, and 5B, consistent with a preferred embodiment.

DETAILED DESCRIPTION OF THE PREFERRED EMBODIMENTS

The disclosed innovations of the present application will be described with particular reference to presently preferred embodiments (by way of example, and not of limitation).

Herein this application, a fraction of the multiphase fluid refers to a numerical value for the weight or volume fraction of the fluid, such as 0.85, for example. This value would correspond to 85%, for example.

Herein this application, a phase of a multiphase fluid refers to a particular phase such as a liquid phase, gas phase, or solid phase. Additionally herein this application, a phase of a multiphase fluid also refers to a particular liquid phase in a multiphase fluid of two or more liquid phases, with or without a gas phase or phases. Additionally herein this application, a phase of a multiphase fluid also refers to a gas phase in a multiphase fluid of two or more liquid phases.

Figure 3:
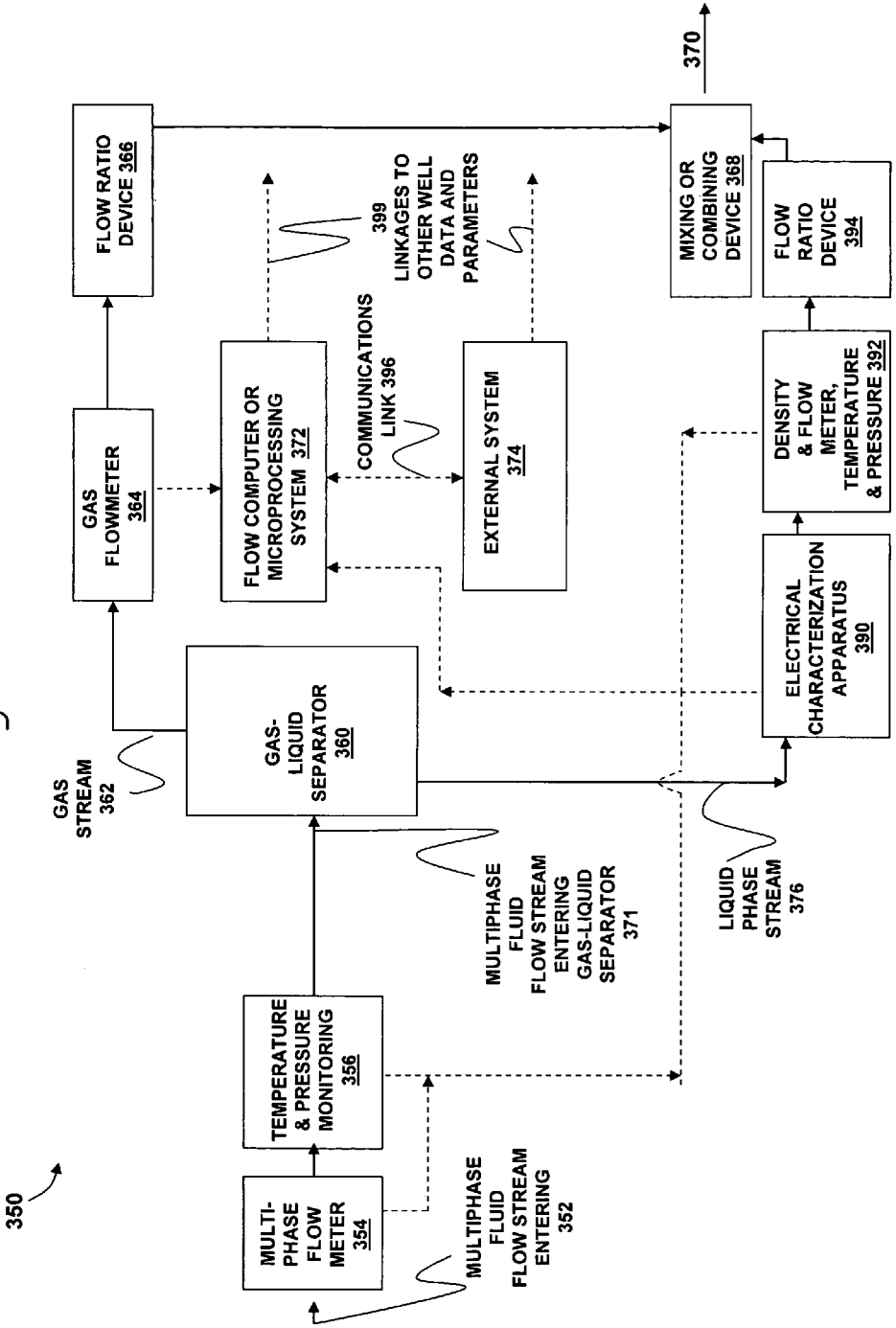
FIG. 3 shows an exemplary multiphase fluid characterization system, consistent with a preferred embodiment.

FIG. 3 shows a multiphase fluid characterization system 350 according to an illustrative, non-limiting example of a preferred embodiment consistent with the present application, for characterizing a multiphase fluid, such as crude petroleum oil. The crude petroleum oil can be a liquid stream comprising oil and an aqueous or water solution, with entrained non-condensed gas. A gas-liquid-liquid multiphase fluid flow stream 352 can enter the system. The flow rate of the total flow stream can be monitored at 354. Pressure of the flow stream can be monitored at 356. As discussed below, many different combinations of mechanical devices and instruments can be used. Multiphase flow stream 371 can enter gas-liquid separator 360 where a condensible and/or non-condensible gas fraction can be separated from the multiphase fluid to a degree consistent with the composition and physical properties of the multiphase fluid and its components, as well as the design and operating parameters of gas-liquid separator 360 as known to a person having ordinary skill in the design and operations of gas-liquid separators. The gas fraction flow stream 362 exits separator 360 and the flow rate, temperature, and pressure, if any, can be monitored at 364. The flow ratio of flow stream 362 can be maintained by a suitable device at 366.

As described earlier, gas-liquid production separators are detailed in Chapter 12 of the third printing of the Petroleum Engineering Handbook. FIGS. 12.23 and 12.25 from the Petroleum Engineering Handbook show schematics of typical production gas-liquid separators as can be used as separator 360.

A liquid fraction flow stream 376 can be electrically measured for water content using an electrical characterization system at 390 and can be monitored for density, flow rate, temperature, and pressure at 392. Flow ratio can be maintained on stream 376 by a suitable device at 394.

Stream 376 and 362 can be combined in mixing or combining device 368 and then exit system 350 as stream 370.

Figure 1:
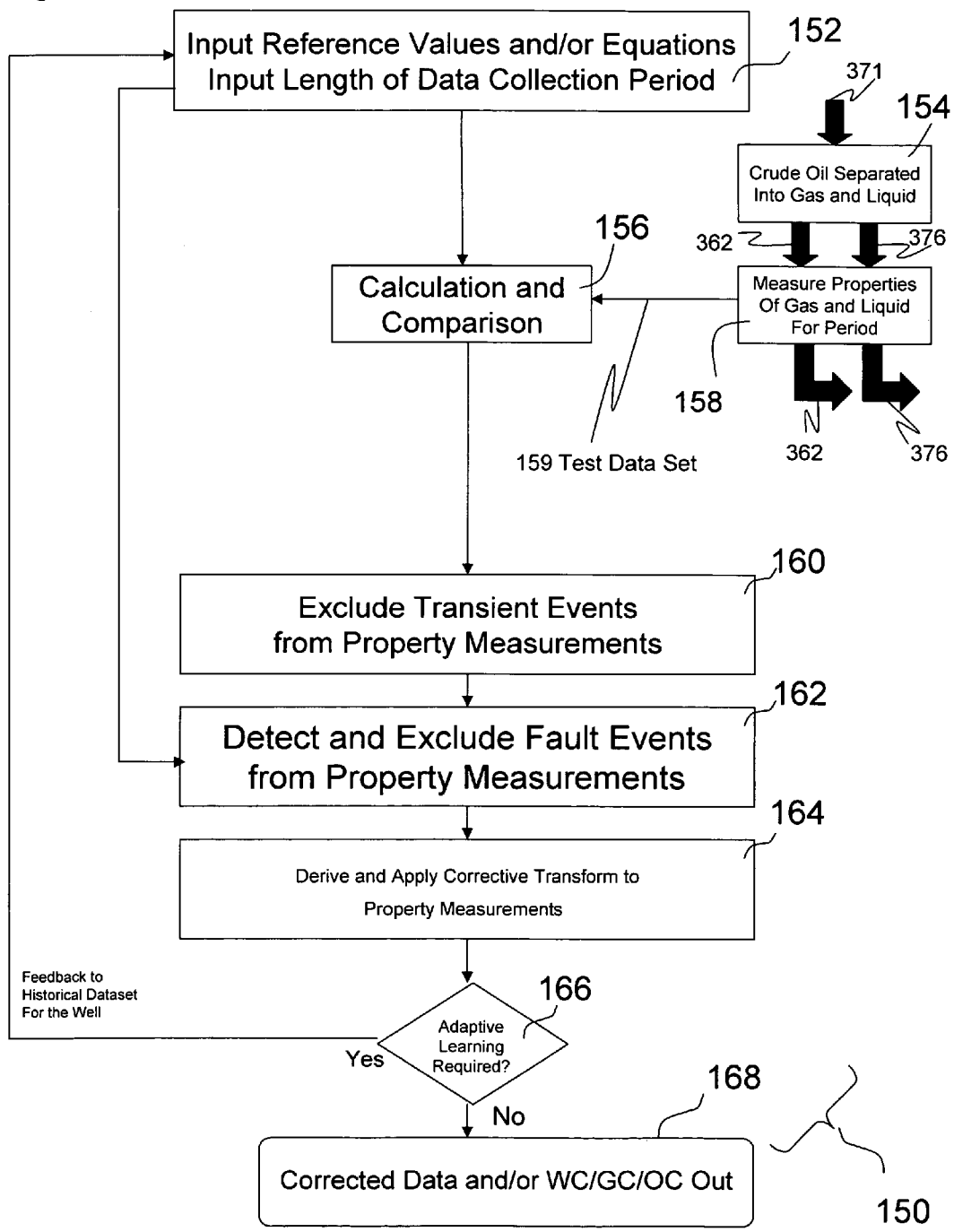
FIG. 1 shows one embodiment of a method for use with the systems of FIGS. 2 and 3, and FIG. 1B, for determining the water cut of crude petroleum oil production, consistent with a preferred embodiment.
Figure 1A:
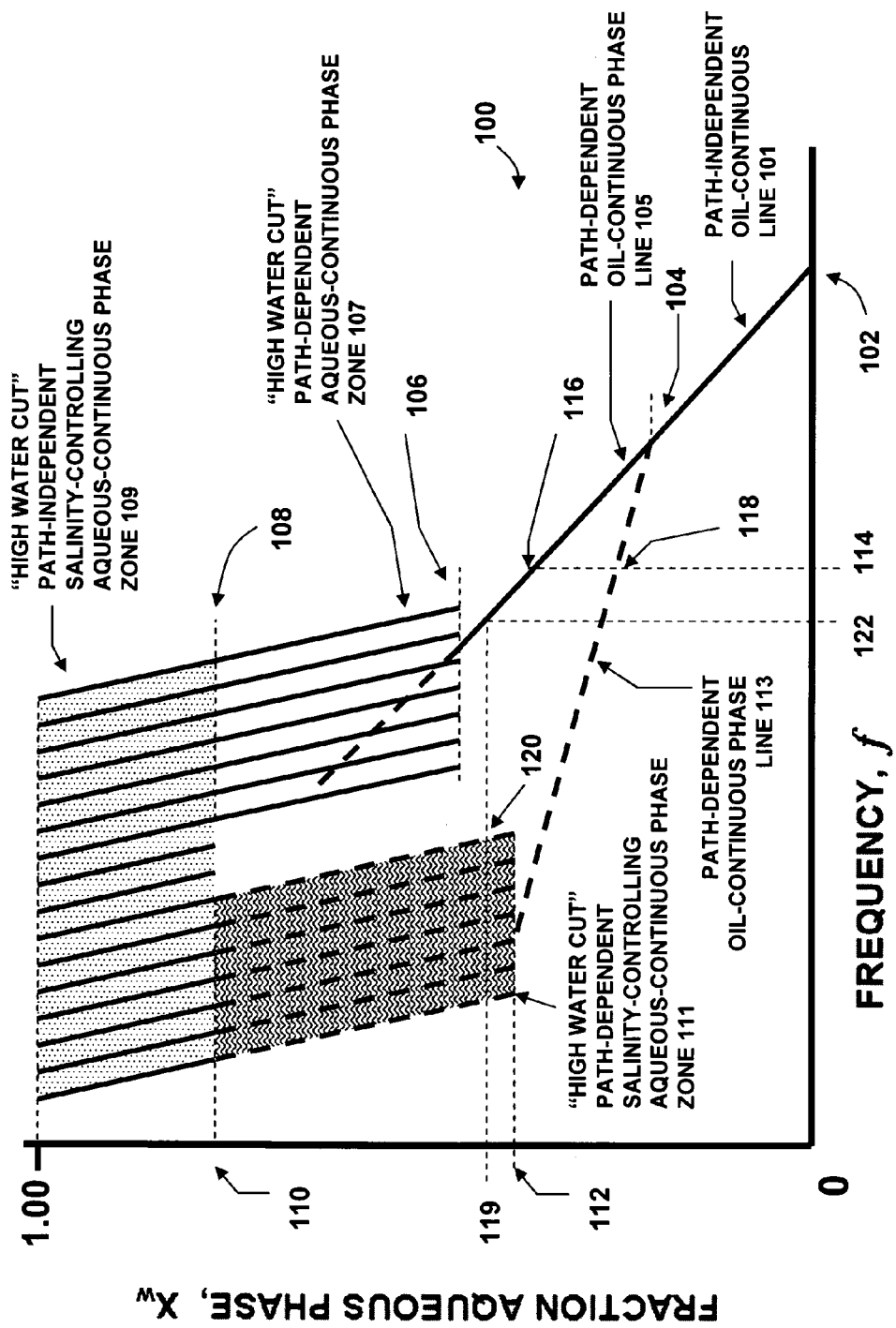
FIG. 1A shows a exemplary phase versus frequency diagram 100 of a particular crude petroleum oil and a range of aqueous solutions of varying salinity as previously described.
Figure 4:
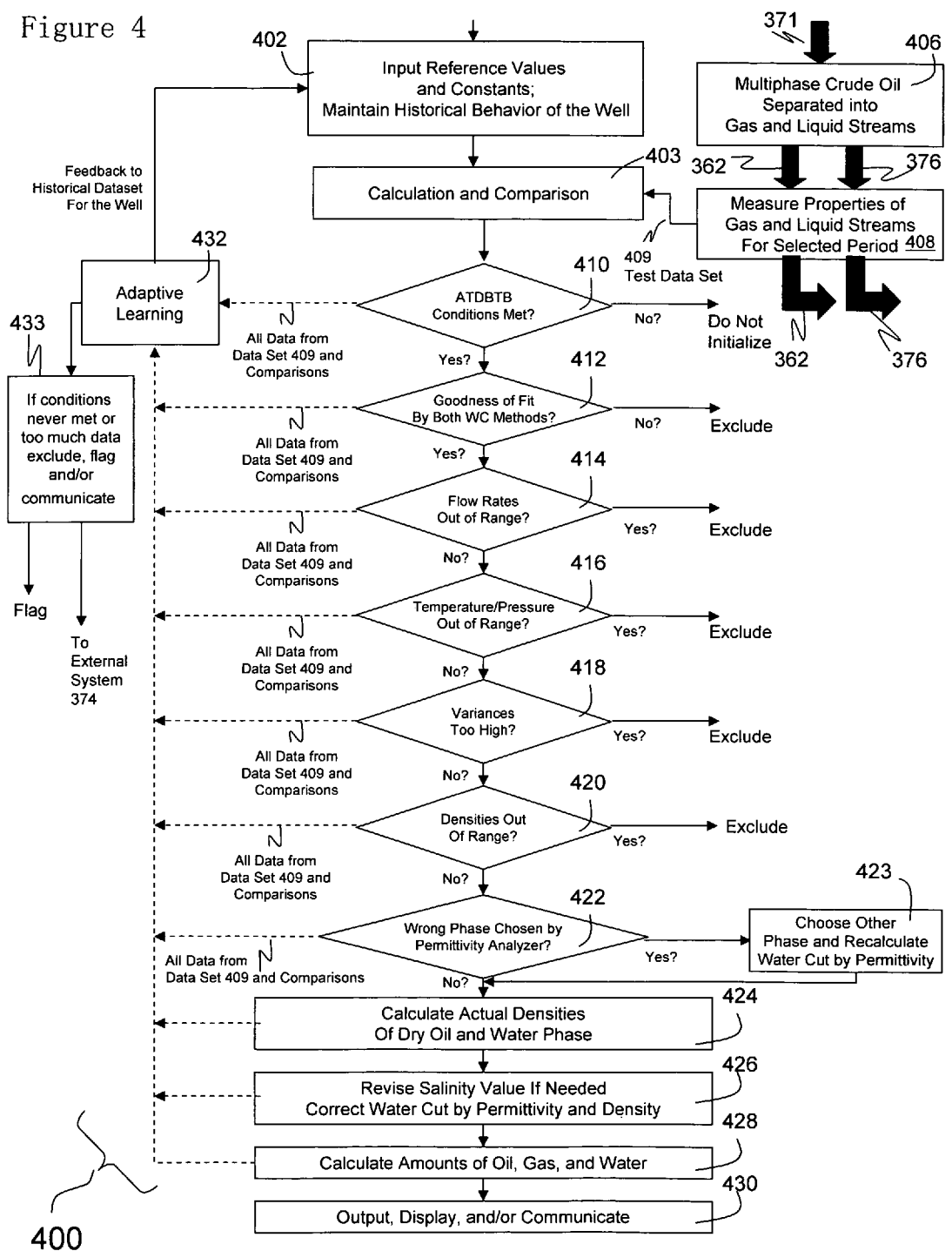
FIG. 4 shows one embodiment of a method used in the system of FIG. 3 and FIG. 1B, consistent with a preferred embodiment.

Measuring components 354, 356, 390, 392, and 364 can all or selectively be electrically coupled (shown as dashed lines on FIG. 3) to flow computer or microprocessor system 372 which in one embodiment, performs and outputs the calculations of, for example, the methods of FIGS. 1 and 4. In another embodiment, flow computer or microprocessor system 372 can transmit or output and display collected measurements to external system 374 where the measurements can be stored or other calculations can be performed, including, for example, the methods of FIG. 1 and 4.

Figure 1B:
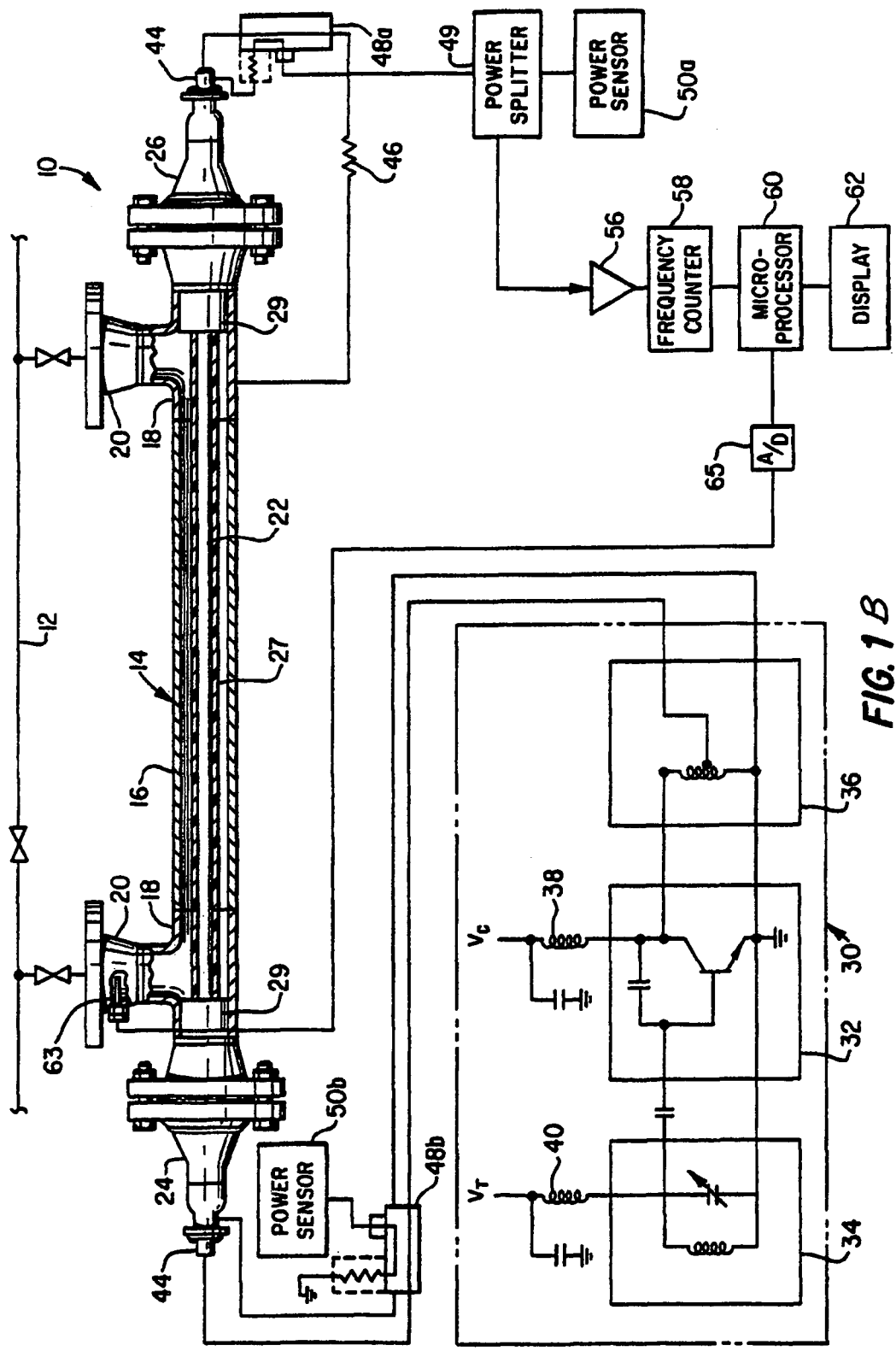
FIG. 1B shows a reproduction of U.S. Pat. No. 4,996,490 FIG. 1 as an example of one embodiment of an electrical characterization apparatus that can perform a water content analysis on a multiphase fluid flow stream.

A water cut electrical characterization system can perform the function of water content measurement in component 390. U.S. Pat. No. 4,996,490 describes some of the preferred embodiments of such a water cut electrical characterization system to be used in the present application. FIG. 1B is a reproduction of FIG. 1 from U.S. Pat. No. 4,996,490 as an example of one embodiment of a microwave analyzer that can be used with the present innovations.

FIG. 1B shows illustrated a diagram of an apparatus for measuring the concentration of one substance or material such as water, in another substance or material such as crude petroleum oil, which is being transmitted as a liquid mixture flow stream through a pipeline. The apparatus is generally designated by the numeral 10 and is particularly adapted for interconnection with a fluid transmission pipeline 12 for sampling the pipeline flow stream. Alternatively, the apparatus 10 might become part of the pipeline. The apparatus 10 includes a fluid flow conducting and measurement section 14 comprising an outer conduit section 16, including spaced apart pipe tee sections 18 having conventional flange portions 20 formed thereon for connection to branch conduit portions of the pipeline 12. The measurement 14 comprises a coaxial transmission line which includes a center conductor 22 preferably formed of a metal such as stainless steel which extends between opposed end support parts 24 and 26 which are described in detail in the above-referenced patent application. The center conductor 22 preferably comprises a generally cylindrical rod or tube member coaxially arranged in the conduit 16 and provided with an outer sheath 27 formed of a material having a relatively low dielectric loss tangent, preferably less than 0.1 at a frequency of 1.0 GHz. The sheath 27 preferably comprises a relatively easy-to-fabricate plastic such as polypropylene, a plastic sold under the trademark Delrin or one of the fluorocarbon plastics. Alternatively, certain ceramics or other materials may also be used as the outer sheath 27 as long as they are low loss tangent dielectric materials. The fit between the outer sheath 27 and the center conductor 22 is preferably a forced or line-to-line fit although some clearance may be permitted as long as fluid flow between the center conductor and the outer sheath is prohibited. In an apparatus where the center conductor has a diameter of 0.25 inches, the outer diameter of the sheath 27 is preferably at least about 0.50 inches or, alternatively, a ratio of the outer diameter of the sheath to the outer diameter of the center conductor is in the range of about two to one.

It has been determined that with the provision of a sheath 27 formed of one of the above-mentioned materials and in the proportions described, that the electrical circuit for propagating microwave radiation through the apparatus 22 retains a high quality signal resolution characteristic in liquid mixtures of oil and water, for example, wherein the water content is relatively high, that is on the order of more than 5% to 10% by volume. With this type of center conductor arrangement, the circuit associated with the apparatus 10 and described herein below retains good field intensity or prevents short circuiting of the center conductor to the outer conductor in an unwanted location, the oscillator circuit retains its good load-pulling characteristics with good resolution of phase and the interface between the sheath 27 and the fluid in the conduit 16 is a new propagation medium which has desirable operating characteristics.

When the apparatus 10 is operating with a liquid composition which is high in water content or a so-called water continuous phase, the conductivity of the composition is high compared to a good dielectric but low compared to a good conductor and, of course, the liquid composition is in direct contact with the wall surfaces of the measurement section 14 including the center conductor. The insulating sheath 27 prevents the radio frequency (RF) energy from being shorted out immediately at the point where the RF energy enters the measurement section or where the fluid cross section begins. Moreover, the sheath 27 now becomes the primary region where the RF field is propagated with the conductive fluid becoming a pseudo outer wall of the measurement section in place of the wall of the conduit 16. The cross sectional measurement of the water-in-oil composition is still preserved due to the large skin depth of the microwave or RF energy at the operating frequency. This skin depth is large through the water as the conducting medium of the outer half of the coaxial transmission line formed by the measurement section. The dielectric structure is now the sheath 27. The properties of the propagated RF energy still reflect the changing content of the oil in the water and this is related through pulling of the unisolated oscillator which is described herein below. The sheath 27 must be thick enough to maintain a reasonable coaxial impedance to be able to propagate the RF energy into the measurement section 14 and maintain a measurement capability. A very thin dielectric coating on the center conductor 22 will cause a very low impedance with a liquid composition having a high water content and therefore the RF energy would be reflected at the fluid interface.

RF energy is not propagated in the interior of a good conductor. The conductor guides the electromagnetic waves. The energy travels in the region between the conductors in a coaxial transmission system with a good dielectric. The currents that are established at the conductor surfaces propagate into the conductor in a direction perpendicular to the direction of the current density. The current density or electric field intensity established at the surface of a good conductor decays rapidly looking into the conductor. When the conductor is resistive or, low conductivity, this depth into the conductor increases rapidly. This phenomenon is known in the art as skin depth.

As shown in FIG. 1B, the center conductor 22 extends through opposed end block members 29 which are also preferably formed of a relatively high insulative material such as a fluorocarbon plastic and the end plug sections are configured in a way similar to the ones described in the above-referenced patent application.

The measurement section 14 is operably connected to a source of radio frequency (RF) or so-called microwave energy comprising an unbuffered or unisolated, free-running oscillator, generally designated by the numeral 30. The oscillator 30 includes an active circuit 32 operably connected to a tuning circuit 34 and to an impedance matching network circuit 36. The circuit 32 is adapted to receive a constant DC voltage, $V_c$, from a source not shown and by way of a filter circuit 38. The tuning circuit 34 is also adapted to receive a controllable DC voltage, $V_t$, from another source, not shown, by way of a second filter circuit 40. The oscillator 30 has an appreciable load-pulling characteristic. The fundamental operating frequency of the oscillator is changed as the complex load is changed on the output circuit of the oscillator. The oscillator 30 is preferably of a type commercially available such as from Avantek Company, Santa Clara, Calif. as their model VTO 8030 voltage controlled oscillator. The exemplary oscillator 30 has a maximum load-pulling characteristic of about 35 MHz at a nominal 200 MHz operating frequency into all phases of a short circuit at the end of a 50 Ohm line stretcher (approximately 0.5 DB return loss). The oscillator 30 is operably connected to the apparatus measurement section 14 through a suitable connector 44 which is in electrically conductive engagement with the center conductor 22 at the end part 24 and at the opposite end of the center conductor 22 through a second connector 44, a resistance 46 and with the outer conductor or conduit 16 as illustrated. The end part 26 is also adapted to connect the center conductor 22 with a 10 DB directional coupler 48a which is operable to sample the microwave energy or power transmitted through the coaxial measurement section 14. The coupler 48a is connected to a power splitter 49 which is connected to a power sensor 50a. The directional coupler 48a may be of a type manufactured by Minicircuits Company of Brooklyn, N.Y. as their model ZED-15-2B. The power splitter 49 may be of a type ZFSC-2-2 also manufactured by Minicircuits. The power sensor 50 may be of a type 437B manufactured by Hewlett Packard of Sunnyvale, Calif.

A second directional coupler 48b is interposed in the circuit between the end part 24 and the oscillator 30 and is connected to a second power sensor 50b. The directional couplers 48a and 48b may be of identical configuration. The coupler 48a is connected to the power splitter 49 which provides an output signal which is amplified by an amplifier 56. The output of the amplifier 56 is adapted to be input to a frequency counter 58 which is also adapted to be connected to a microprocessor 60. A suitable digital display or readout device 62 is connected to the microprocessor 60. The amplifier 56 may be of a type commercially available from the above-mentioned Minicircuits Company as their model ZFL-500. The frequency counter 58 may be of a type manufactured by Hewlett Packard Company as their model 5342A and the microprocessor 60 may be a Hewlett Packard type 9836. The system illustrated in FIG. 1 preferably includes a temperature compensation circuit including a thermocouple 63 operably connected to a conversion circuit 65 to provide a suitable digital signal to the microprocessor 60.

In operation, the changing dielectric constant presented by the material flowing through the measurement section 14, such as caused by the presence in a liquid mixture, for example, of varying amounts of water in oil or oil in water, causes the oscillator 30 to change its operating frequency over a relatively narrow frequency band as compared with the nominal operating frequency of the oscillator. For example, the oscillator 30, in a preferred form, can be pulled from its nominal operating frequency through a range of about 20 MHz by the changing dielectric constant of the medium flowing through the measurement section 14.

Figure 2:
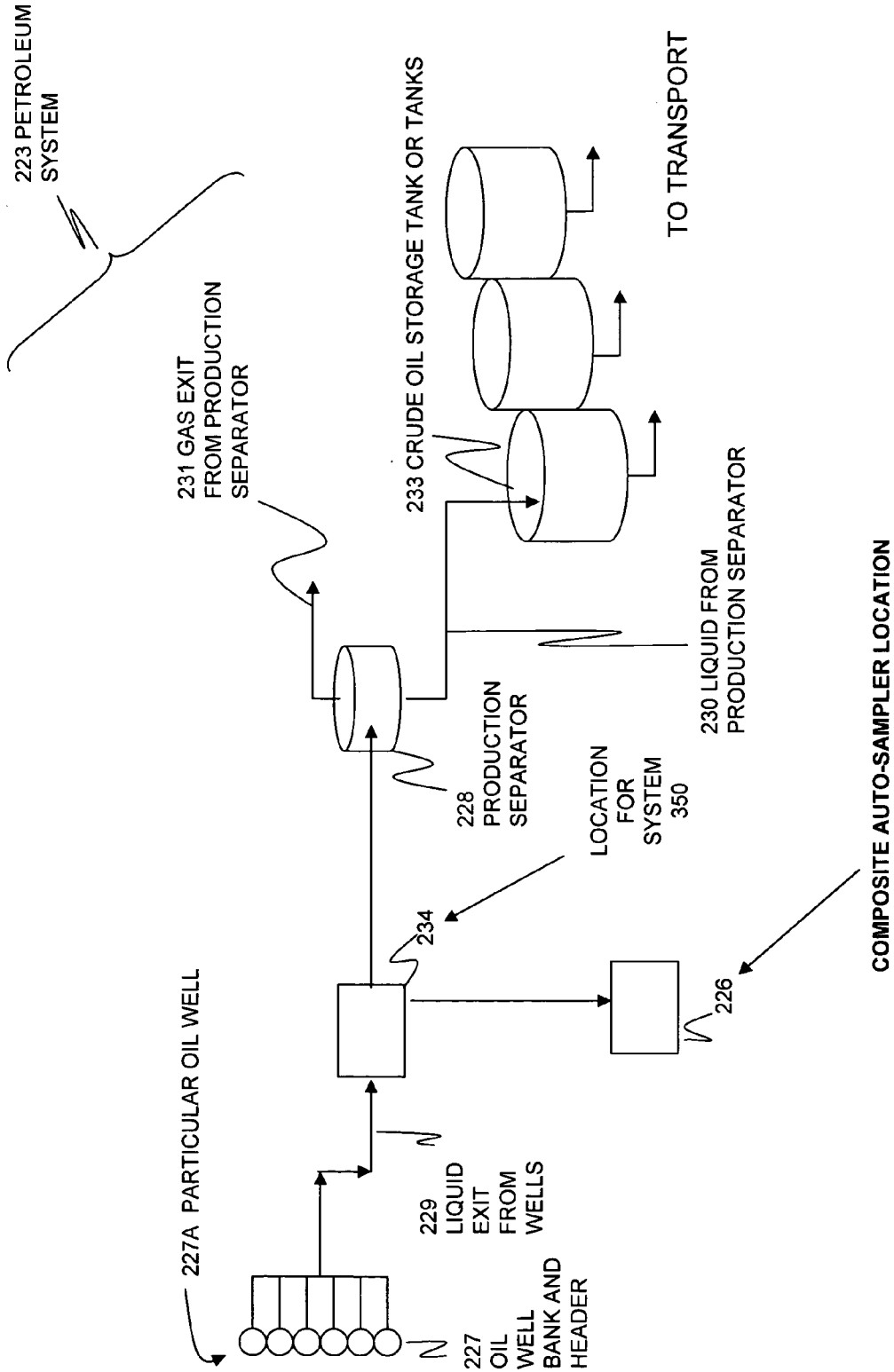
FIG. 2 shows an exemplary petroleum processing and transportation system, consistent with a preferred embodiment.

FIG. 2 shows an exemplary petroleum production, processing, characterization, and storage system 223 according to an illustrative, non-limiting embodiment consistent with the present application in which the multiphase fluid characterization system 350 can be incorporated. A pipeline 229 leads from a set of petroleum-producing wells 227 or a given well 227A which all or some may be located on land or under-sea. The pipeline 229 can lead to the multiphase fluid characterization system 350, positioned at point 234 between wells 227 and oil-water production separator 228. An auto-composite sampler 226 can be positioned either before or after system 350 at point 234. The stream in pipe 230 represents the separated liquid phase leaving the liquid-gas separator 229 whereas stream 231 is the separated gas leaving the separator. The contents of storage tank or tanks 233 can then be transported.

FIG. 1 shows a method according to one embodiment of the disclosed innovations for determining the water cut, gas cut, and oil cut of crude petroleum oil production. In one embodiment, the method of FIG. 1 collects a time series of fluid property data on a multiphase fluid flow stream (step 158), such as can be flowing in pipeline 229 using the characterization system 350. All of these measured values can then be stored in the memory of the computer or microprocessor system 372 and can then be used to implement the other method steps in FIG. 1. In one embodiment, the values can also be communicated to an external system 374 via link 396 for various operations such as storage, processing, data manipulation, transform development, and auto-calibration or correction of raw data via the transforms by implementing some or all of the steps of the method of FIG. 1 on external system 374. In various embodiments, the time series of measurements can include flow rate of the multiphase fluid discharging from the well, temperature of said multiphase fluid, pressure of said multiphase fluid, gas fraction of said multiphase fluid, density of the gas fraction after it is separated in a gas-liquid separator prior to its characterization, liquid level in gas-liquid separator 360, liquid fraction of said multiphase fluid, flow rate of said liquid fraction, density of said liquid fraction, water cut of said multiphase fluid by both the density method and the electromagnetic characterization method, electromagnetic measurements corresponding to permittivity of said liquid fraction, flags of equipment or devices out-of-range in measurement capability, and electromagnetic power loss measurements through said liquid fraction using apparatus 390.

In one embodiment, step 160 filters the time series of data from step 158, according to a set of filtering parameters. In various embodiments the filters can remove data points that are uncharacteristic of the performance of the well at that particular time in the operational history or cycle of the well.

In one embodiment, step 160 removes start-up data in which the well is momentarily disturbed as it is switched into test mode. This is conventionally known as the "Delay Before Test Begins" (DBTB). In one embodiment, the DBTB value can be entered manually. In one embodiment, the value can be dynamically calculated by the method of FIG. 1. During the start-up, a large part of the variability in the measurements are caused by the switching action to direct a particular well to a test system, such as system 350, and the variability during the start of the test is not characteristic of the well at steady state.

In one embodiment of the use of the method of FIG. 1, a well is re-started after being held in a dormant or non-producing state. Start-up of such a well can have a start-up period requiring a DBTB of tens of minutes to several hours.

In some embodiments, wells which never reach steady state can be tested using the method of FIG. 1.

In some embodiments, the filtering action of step 160 excludes data points from the time series.

In one embodiment, step 160 includes auto-calibration routines to correct at least some of the measurements prior to filtering. In one embodiment, step 160 can derive and apply corrective transforms using the methods of U.S. Patent Applications 60/700,790, 60/721,233, 60/627,436 and Ser. No. 11/273,613. In one embodiment, the corrective transform can be applied to at least one of the plurality of measurements resulting from step 158.

In one embodiment, step 160 removes measurements in which the measurement is out of range of range for the particular device conducting the measurement.

In various embodiments, the filtering parameters in step 160 can include upper and/or lower limits for the various measurements in the time series, or for statistical parameters calculated from those measurements. In some embodiments, these statistical parameters can be boxcar variances of measurements in the time series, a boxcar of the standard deviations of the measurements, a boxcar of the means of the measurements, a boxcar of the averages of the measurements, a boxcar of the derivatives of the of the measurements, a boxcar of the total number of excluded measurements from the time series, a boxcar of the maximums of measurements, a box car of minimums of measurements, and flow weighted averages of the measurements of the time series, or various combinations thereof.

In some embodiments in step 160, the boxcar represents a total of the data values within the boxcar. In some embodiments, the boxcar represents an average of the data values within the boxcar. In some embodiments, the boxcar represents the mean of the values within the boxcar.

In some embodiments, the boxcar can contain as few as 2 data time points. In some embodiments, the boxcar can be a running statistic for the complete steady state history of the well.

In some embodiments, the upper and/or lower limits of step 160 can be fixed, dynamically updated, or calculated.

In other embodiments, step 160 can compare the time series of measurements to a model of the multiphase flow behavior, can calculate a deviation value for each time point to determine "outlier" data, if any, and then can perform the filtering action using statistics as previously described. In one embodiment, the model can be developed from past historical performance of the well.

In one embodiment, step 162 assesses the data quality of a filtered subset of the time series of measurements from step 158. In one embodiment, an overall data quality index is calculated.

In a preferred embodiment of step 162, the water cut by electromagnetic characterization and the water cut by density are assessed for agreement with each other as a measure of overall data quality for the test. In one embodiment, the difference is calculated between both water cut methods for each data time point. The average, the standard deviation, and the maximum difference is calculated and determined for all of the differences in the filtered time series. One skilled in the art of statistical calculations and comparisons for two devices making the same measurement has knowledge of many other statistical techniques to be applied to or used in step 162.

In one embodiment, this can be an average, weighted average, or normalized average of the variances or standard deviations for a particular selection of measurements. For example, this would be composed of calculations of a statistical parameters for all the values of a particular measurement, such as the variance or standard deviation of a particular measurement.

In one embodiment, step 162 can use fixed, calculated, or dynamically calculated upper and lower limits for acceptable quality for a particular measurement. In step 162, the method can then count or total the number of deviations above the upper and below the lower limits and use the total number of outliers as one embodiment of assessing the data quality.

In one embodiment, step 162 can calculate a mean, mode, or average value for the filtered measurements of a particular kind, and then use a plus/minus percentage band of acceptability about the mean or average, in order to determine the total number of data points outside the acceptable band.

In step 164, the data quality acceptability is assessed. In one embodiment, the mean, standard deviation, variance, and maximum difference between the two water cut method determinations across the filtered time series are compared against historical values for that particular well judged by experts as being acceptable for overall data quality.

In step 164, if the data quality is not acceptable, in one embodiment, extra data is collected and the method is repeated. In one embodiment, the test is repeated.

In step 164, if the data quality is acceptable, the method of FIG. 1 outputs at least one characterization output, such as the water cut by electromagnetic characterization using step 168. In one embodiment, flow weighted averages for the water cut, gas cut, and oil cut can be outputted by step 168. In a preferred embodiment, flow weighted averages for the total amounts of water, gas, and oil can be outputted by step 168, where the water cut by electromagnetic characterization is used to calculate the water and oil amounts. In a preferred embodiment, flow weighted averages for the production rates of water, gas, and oil can be outputted by step 168, where the water cut by electromagnetic characterization is used to calculate the water and oil production rates.

In step 166, in one embodiment, the method of FIG. 1 then selectively adjusts the filtering parameters. In a preferred embodiment, the method of FIG. 1 has maintained historical average water, oil, and gas production rates from previous tests, along with the corresponding statistical parameters for the data quality assessment performed in steps 162 and 164. In one embodiment, the history is considered since the last work-over of the well, if the well has been worked-over. In one embodiment, the average decline is calculated between each of the tests in step 166. In one embodiment, the expected average daily production for the next test is calculated, along with upper and lower production limits and the expected statistical performance of each water cut determination method and between those methods as previously described. In one embodiment, these expected values are based on a model of how those values change over time and amount of water, oil, and gas produced from the well.

FIG. 4 shows a method according to one embodiment of the disclosed innovations for determining the oil cut, gas cut, and water cut of crude petroleum oil production, and more particularly, the estimated production output and production rate from the particular well being tested. In one embodiment, in step 402, historical well performance, historical statistics such as filtering parameters, reference values, data sets, parameters, or equations or models which have been fitted to those values, or data sets, or lookup tables, can be maintained and/or inputted for use by the method of FIG. 4, such as in the calculations, comparisons, exclusions, derivations and applications of corrective transforms by computer or microprocessor system 372, or various combinations thereof.

In one embodiment, a multiphase crude oil flow stream 371 can be separated into a gas stream 362 and a liquid stream 376 as previously described, and shown in FIG. 4 as step 406 as would be performed in separator 360. In one embodiment, the method of FIG. 4 in step 408 can make and collect electromagnetic characterization measurements of the water cut on stream 376 using electrical characterization apparatus 390, densitometer measurements of the mixture density and the flow rates of stream 376 measured by the on-line densitometer 392, and gas conditions and flow rates on stream 362 using gas flow meter 364. The liquid level in separator 360 can also be measured and collected in the time series of data resulting from step 408.

In one embodiment, all of these measured values as test data set 409 from step 408 can then be stored in the memory of the computer or microprocessor system 372 and can then be used to implement the other method steps in FIG. 4. In one embodiment, the values can also be communicated to an external system 374 via link 396 for various operations such as storage, processing, data manipulation, transform development, and correction of raw data via the transforms by implementing some or all of the steps of the method of FIG. 4 on external system 374.

In one embodiment, step 403 of method of FIG. 4 can calculate the water cut by density for each time point, the water cut by electromagnetic characterization for each data point, and various characterizations and parameters, including adapting the time delay for exclusion of data based on historical data, using the time series of measurements from test data set 409 for water cut data and flow rate data, and optionally, information and values from input step 402. In some embodiments, other electrical properties and physical or non-electrical properties can be read and collected in step 408 for other kinds of calculations and comparisons in step 403.

In one embodiment, the method of FIG. 4 can conduct an Auto-Calibration and Correction 470, as steps 410 and 412, by deriving and applying at least one corrective transform using the method or methods of U.S. Patent Applications 60/700,790, 60/721,233, 60/627,436 and/or Ser. No. 11/273, 613. In one embodiment, the corrective transform or transforms can be applied to at least one of the plurality of measurements or calculated measurements resulting from steps 403 and/or 408.

In one embodiment, in step 414, the method of FIG. 4 can do an Initialization Check 480, by comparing the corrected data set from step 412 to determine if the well is behaving within the adaptive time delay before test begins ("ATDBTB") constraints as inputted in step 402 and/or as calculated in steps 403 and 432 and/or fed back to the historical database of characteristic well behavior, or various combinations thereof. If the well has not "settled down" within the particular constraints, the initialization of the test can be delayed in step 415, thus excluding data points until initialization is achieved. This test can be made sequentially against all data points in data set 409.

In one embodiment, an adaptive exclusion time window can be imposed on data set 409 as another embodiment of step 414 to exclude data if an upset occurs during the test, until steady state or characteristic operation is re-established.

In one embodiment, in step 416, the method of FIG. 4 can perform a Phase Selection Mistake Correction check 485 by comparing the water cut by electromagnetic characterization to the water cut by density against an acceptance tolerance inputted in step 402 for each time point to insure that the microwave analyzer properly chose the correct phase under the method of U.S. Pat. No. 4,996,490 as previously described. If the difference between both methods is not within the tolerance, the choice of phase by the microwave analyzer is changed and the water cut by electromagnetic characterization is recalculated in step 417. In one embodiment, the difference between both methods is checked again in step 418 against the acceptance tolerance. In one embodiment, if the difference is still not within tolerance, the data point is excluded by step 418.

Starting with step 419, in one embodiment, the method of FIG. 4 can perform a series of Out of Range Checks and Exclusions 490 for various operating parameters. As a non-limiting example, the method of FIG. 4 performs such checks in steps 419, 420, 424, and 426.

In one embodiment, in step 419, the method of FIG. 4 can examine the remaining data set from step 416 or step 418 to determine if the gas-liquid separator 360 has acceptable liquid level. If a particular time point is not within the liquid level constraints for the separator, it can be excluded from the data set from steps 416 or 418, and an upset condition can be established in the data set. In other words, the data point represents a time point where the separator has unacceptably deviated from steady state or characteristic operation according to the inputted or calculated constraints. This test can be made against all data points in the data set from step 416 or step 418. In a preferred embodiment, an adaptive exclusion time window can be imposed on the data set to exclude data until steady state or characteristic operation for liquid level in the separator is re-established.

In one embodiment, in step 420, the method of FIG. 4 can examine the remaining data set from step 419 to determine if the well is behaving within the range of acceptable temperatures and/or pressures per limits inputted in step 402 and/or as calculated in steps 403 and 432 and/or fed back to the historical database of characteristic well behavior, or various combinations thereof. If a particular time point is not within the constraints, it can be excluded from the data set and an upset condition can be established in the data set. In other words, the data point represents a time point where the well has unacceptably deviated from steady state or characteristic operation according to the inputted or calculated constraints. This test can be made against all data points in the data set from step 419. In a preferred embodiment, an adaptive exclusion time window can be imposed on the data set to exclude data until steady state or characteristic operation for temperature and pressure is re-established.

In one embodiment, in step 424, the method of FIG. 4 can examine the data set from step 420 to determine if the gas-liquid separator is producing gas and liquid streams 362 and 376 with acceptable densities per limits inputted in step 402 and/or as calculated in steps 403 and 432 and/or fed back to the historical database of characteristic well behavior, or various combinations thereof. If it a particular time point is not within the constraints, it can be excluded from the data set and an upset condition can be established in the data set. In other words, the data point represents a time point where the gas-liquid separator 360 has unacceptably deviated from steady state or characteristic operation according to the inputted or calculated constraints. This test can be made against all data points in the data set from step 420. In a preferred embodiment, an adaptive exclusion time window can be imposed on the data set from step 420 to exclude data until steady state or characteristic operation is re-established. For example, high densities in the gas phase might indicate that the gas-liquid separator 360 is not performing adequately because liquid phase carryover is being entrained in the gas phase. In the alternative, low densities in the liquid phase might indicate that the gas-liquid separator 360 is not performing adequately because gas phase carry-under is being entrained in the liquid phase.

In one embodiment, in step 426, the method of FIG. 4 can examine the data set from step 424 to determine if the well is behaving within the range of acceptable flow rates or within the turn-down limits of all flow meters pre those inputted in step 402 and/or as calculated in steps 403 and 432 and/or fed back to the historical database of characteristic well behavior, or various combinations thereof. If it a particular time point is not within the constraints, it can be excluded from the data set from step 424 and an upset condition can be established in the data set. In other words, the data point represents a time point where the well has unacceptably deviated from steady state or characteristic operation according to the inputted or calculated constraints. This test can be made against all data points in the data set from step 424. In a preferred embodiment, an adaptive exclusion time window can be imposed on the data set to exclude data until steady state or characteristic operation is re-established.

In one embodiment, data subset 409A results from step 426. This data subset has now been corrected via steps 470 and 485, and filtered via steps 480 and 490.

In one embodiment, in steps 427 and 428, the method of FIG. 4 performs a data quality assessment 495 on data subset 409A. In one embodiment, an overall data quality index is calculated.

In a preferred embodiment, the water cut by electromagnetic characterization and the water cut by density are assessed for agreement with each other as the measure of overall data quality for the test. In one embodiment, the difference is calculated between both water cut methods for each data time point. The average, the standard deviation, and the maximum difference is calculated for all of the differences in 409A. One skilled in the art of statistical calculations and comparisons for two devices making the same measurement has knowledge of many other statistical techniques to be applied to steps 427 and 428.

In one embodiment, this can be an average, weighted average, or normalized average of the variances or standard deviations for a particular selection of measurements. For example, this would be composed of calculations of a statistical parameters for all the values of a particular measurement, such as the variance or standard deviation of a particular measurement.

In one embodiment, steps 427 and 428 can use fixed, calculated, or dynamically calculated upper and lower limits for acceptable quality for a particular measurement. In steps 427 and 428, the method can then count or total the number of deviations above the upper and below the lower limits and use the total number of outliers as one embodiment of assessing the data quality.

In another embodiment, steps 427 and 428 can calculate a mean, mode, or average value for the filtered measurements of a particular kind, and then use a plus/minus percentage band of acceptability about the mean or average to determine the total number of data points outside the acceptable band.

In steps 427 and 428, in one embodiment, the mean, standard deviation, variance, and maximum difference between the two water cut method determinations across the filtered time series are compared against historical values for that particular well judged by experts as being acceptable for overall data quality.

In step 428, if the data quality is not acceptable, in one embodiment, extra data is collected per step 434 and the method is repeated by returning to step 408. In one embodiment, the total test is repeated.

In one embodiment, step 429 can check to determine if too many iterations of data collection are made and/or if too much data has been excluded from data set 409. This checks, in one embodiment, can be made against expert determinations of iteration limits or percentage of data excluded limits.

In step 428, if the data quality is acceptable, the method of FIG. 4 outputs at least one characterization output, such as the water cut by electromagnetic characterization using step 438. In one embodiment, flow weighted averages for the water cut, gas cut, and oil cut can be calculated and outputted by steps 430 and 438. In a preferred embodiment, flow weighted averages for the total amounts of water, gas, and oil can be calculated and outputted by steps 430 and 438, where the water cut by electromagnetic characterization is used to calculate the water and oil amounts. In a preferred embodiment, flow weighted averages for the production rates of water, gas, and oil can be calculated and outputted by steps 430 and 438where the water cut by electromagnetic characterization is used to calculate the water and oil production rates.

In step 432, in one embodiment, the method of FIG. 4 then selectively adjusts the filtering parameters. In a preferred embodiment, the method of FIG. 4 has maintained historical averages for water, oil, and gas production rates from previous tests, along with the corresponding statistical parameters for the data quality assessment performed in steps 427 and 428. In one embodiment, the history is considered back to the last work-over of the well, if the well has been worked-over. In one embodiment, the average decline is calculated between each of the tests in step 432. In one embodiment, the expected average daily production for the next test is calculated, along with upper and lower production limits and the expected statistical performance of each water cut determination method and between those methods as previously described. In one embodiment, these expected values are based on a model of how those values change over time and amount of water, oil, and gas produced from the well.

In a preferred embodiment, data can be excluded from the data set to be processed by first excluding data using an adaptive delay before test begins ("ATDBTB") conditions not met per step 414. Then using a boxcar technique, data can be excluded using a two sigma window to flow rates out of range per step 426, temperature and pressure out of range per step 420, and optionally, densities out of range for both liquid and gas per step 424.

In one embodiment, if the exclusion conditions for any one or combinations of steps 414, 419, 420, 424, and 426 are never met or they exclude so much data as to not provide for a representative or required period of time for well production measurement, this event can be flagged via step 434 to an operator or sent via external communications link 396 to allow for a notification or manual corrective action.

In a preferred embodiment, adaptive adjustment and learning of the exclusion conditions can be made. In a preferred embodiment, one or more of the steps of the method of FIG. 4 can be done near-real time while the data and measurements are being read in step 408 and optionally adjusts, lengthens, or stops the data collection period to assure that enough representative data is gathered for an adequate well test.

In a preferred embodiment, the method of FIG. 4 can output the an quality overall index, as an indication of the goodness of the test.

EXAMPLE 1

As an illustrative, non-limiting example, a preferred embodiment of the present invention can be applied to determine the water cut of a production well that had just been switched into service. FIG. 5 shows a time series of water cut measurements (501) over a 73 minute period for a particular well 227A and testing system 350 as shown in FIGS. 3, 1B, and 2 using some of the innovations of the methods of FIGS. 1 and 4. The well had been tested before and a manual determination of the Delay Before Test Begins ("DBTB") had been made at 30 minutes as shown on FIG. 5 at 502. Note that the well actually behaved reasonably well during the first 18 minutes as would be judged by a person having ordinary skill in the art of statistics of time series when looking at the points within zone 504 relative to the rest of points of time series 501. However, at minute 19 the well became erratic and did not settle down until about minute 30, as shown by zone 506 points. In one embodiment of the innovations of the present Application, the manual DBTB can be treated as the bare minimum for the ATDBTB by the methods of FIG. 1 and/or FIG. 4.

FIG. 5A shows a set of running boxcar averages of statistical variance of 10, 15, and 20 minutes of data within the three exemplary boxcars 550A. The 73 minute time period was divided by a person having ordinary skill in the art of time series statistics into four sub-periods as 552A, 554A, 556A, and 558A. Such a person can clearly see that the variance generally decreases across the four periods. During period 558A the well had settled down to a variance under 30 as shown on FIG. 5A for all boxcar variances. One of ordinary skill in the art of statistics of time series will also see that the variance of the boxcar tends to decrease as the boxcar duration gets longer, but that all three box cars peak at the roughly 26 to 32 minute time points. As the variances drop on FIG. 5A, the well is said to have been "settling down."

In a preferred embodiment, an adaptively established maximum variance can be established for which a particular well, based on its historical performance, must fall below for the ADTBTB constraints to be met, to allow initialization of data inclusion to determine an average property or properties of the crude petroleum oil flow stream.

Figure 5B:
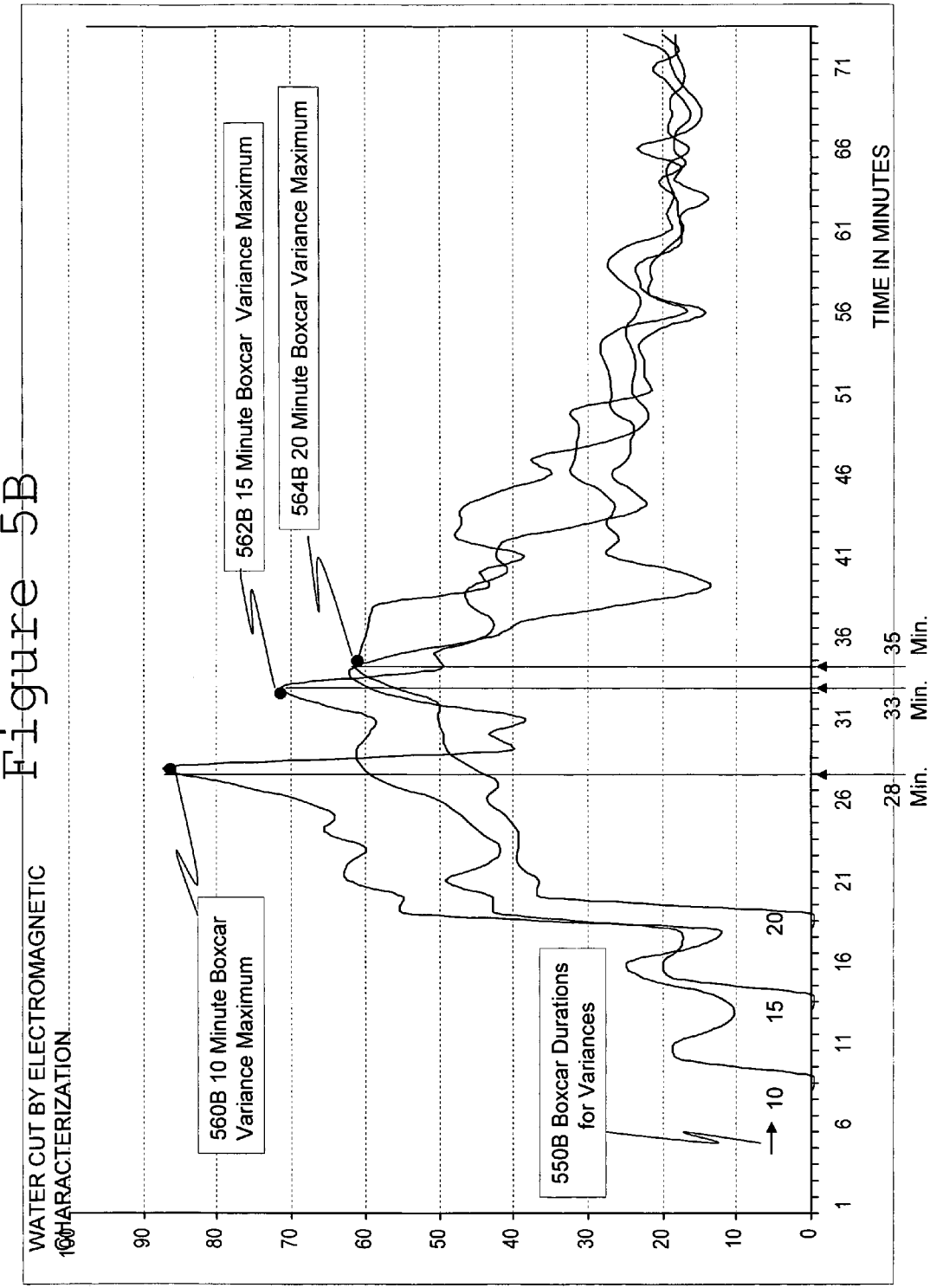
FIG. 5B shows the same variance data as FIG. 5A but with the data smoothed and the maximas of the variance profiles marked, consistent with a preferred embodiment.

FIG. 5B shows the same data as FIG. 5A except that the data is smoothed and the maximums of the three 550B box cars are shown as points 560B, 562B, and 564B, corresponding to time points 28, 33, and 35 minutes, respectively.

FIG. 5C shows a table of statistics for the four periods of FIG. 5A. FIG. 5C first shows that the average maximum between the three box car periods of 10, 15, and 20 minutes was 32 minutes. In this example, the methods of FIG. 1 and FIG. 4 can select this as the ATDBTB, adapting the delay from 30 minutes, as set manually, to 32 minutes based on this particular strategy for determining ATDBTB. In particular, the method of FIG. 4 can calculate this value in steps 403 and test meeting the value on the data set at step 414. FIG. 5C then shows how the average box car variance actually increases from period 552A to period 554A while the actual average water cut percentage difference between period 554A and period 1B is only 0.104% which is within the range of the two most accurate ASTM off-line measurement error rates. Thus, the data within period 554A is usable and would not need to be excluded. FIG. 5C also shows that the particular ATDBTB strategy used in this example that arrived at using the last 41 data points arrived at a value of 62.451% water cut with an average variance of 28.424, which is only 0.016% different that the value for the last period 556B which has a water cut % of 62.525, with a relatively low variance of 19.608. This demonstrates that very accurate determinations of water cuts can be achieved while not waiting for the average variance to achieve a steady state value.

EXAMPLE 2

Figure 6:
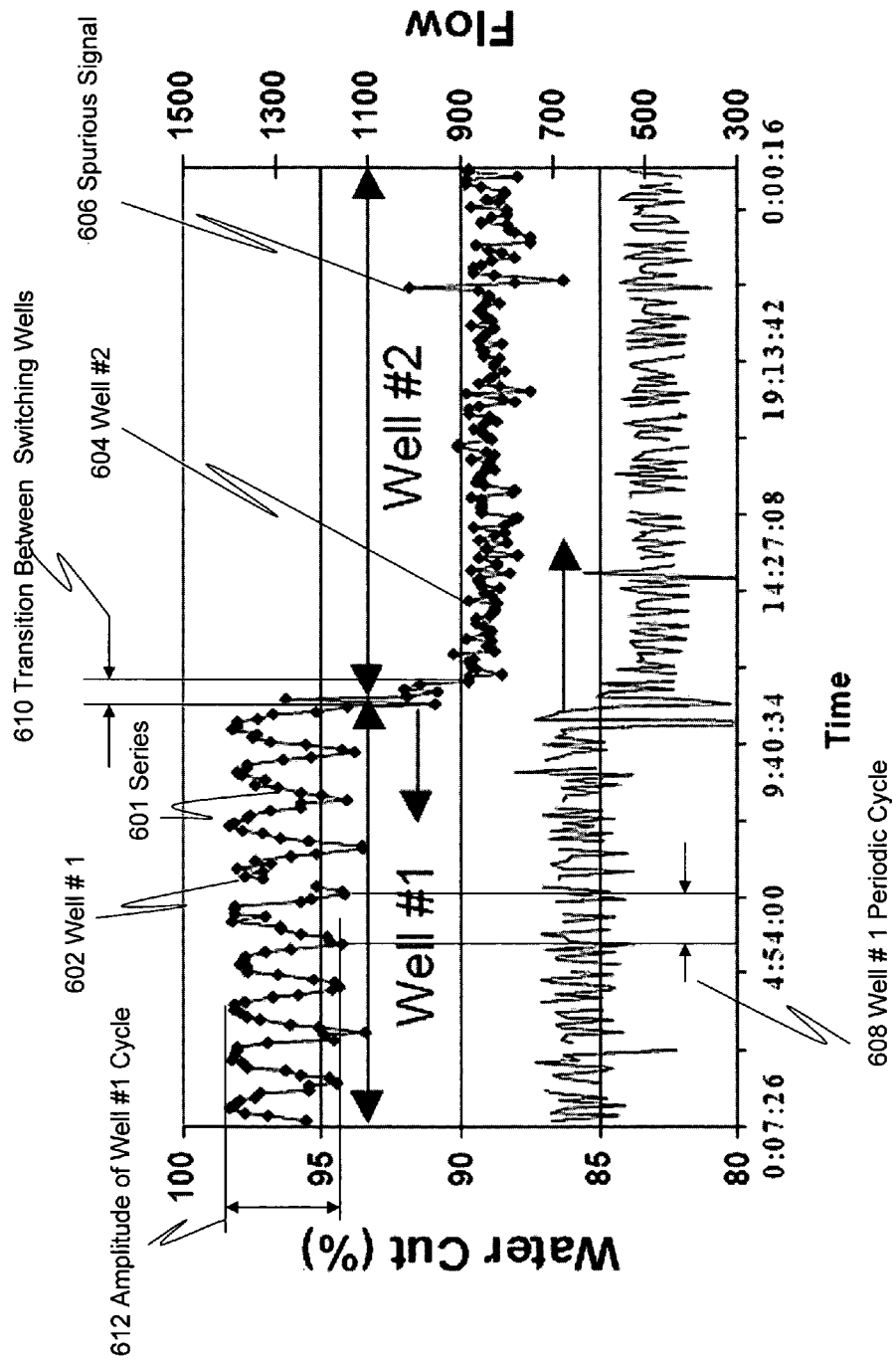
FIG. 6 shows the actual water cut profile and the flow rate profile data from another well test where two wells were tested, consistent with a preferred embodiment.

As another illustrative, non-limiting example, a preferred embodiment of the present invention can be applied to determine the water cut of a production well that cycles as a steady state operation. FIG. 6 shows a time series of water cut measurements (601) over a 73 minute period for a particular well 227A and testing system 350 as shown in FIGS. 3, 1B, and 2 using some of the innovations of the methods of FIGS. 1 and 4. FIG. 6 shows a switch was made between testing Well #1 602 and Well #2 604 and shows a transition period 610 which can be subjected to the methods of FIG. 1 and FIG. 4, or other embodiments, to determine the ATDBTB value. Note also that spurious water cut signal 606 in Well Test #2 could be filtered out using any one of commonly known signal filtering techniques known to a person having ordinary skill in the art of signal filtering.

Of interest is Well Test #1 which shows very cyclic behavior that obviously has a higher variance in percentage water cut than Well #2, as would be judged by one having ordinary skill in time series statistics. Yet, the regularity of the cycle suggests this is not un-steady state but is in-fact the characteristic behavior of that particular well. For example, a cycling intermittent gas lift might cause such behavior. The regularity of wave amplitude 612 and period 608 suggests steady-state wave behavior. Step 402 could maintain, and periodically update, a historical model of the well behavior which fit a sinusoidal wave or wavelet equation to historical data. In one embodiment, step 403 could calculate additional waveform characterizations.

EXAMPLE 3

Figure 7:
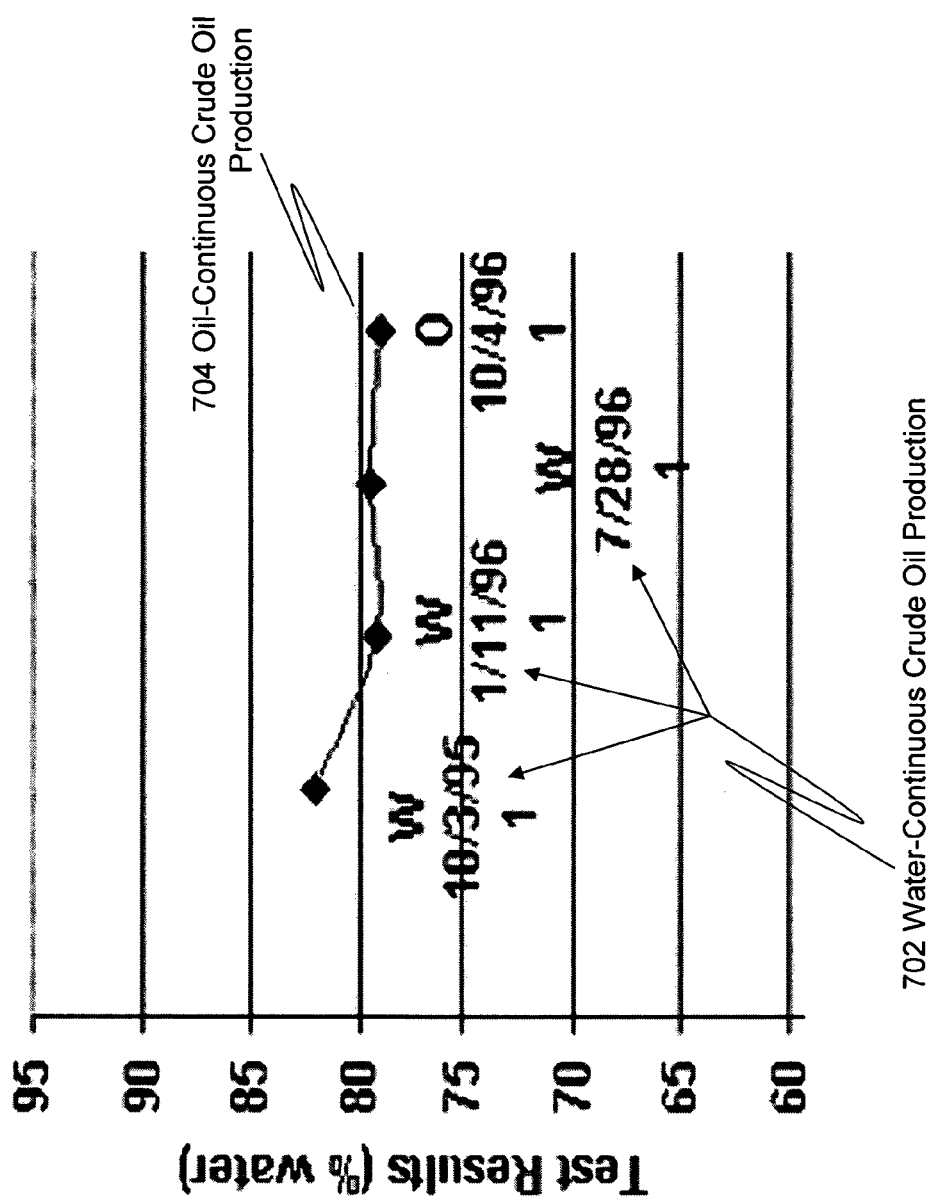
FIG. 7 shows the actual water cut results and phase determination results for yet another well over a one year period, consistent with a preferred embodiment.

As another illustrative, non-limiting example, a preferred embodiment of the present invention can be applied to determine the water cut of a production well that changes water and oil phase characteristics. FIG. 7 shows actual data for a one year period of operation for a particular well where water cut generally dropped over time, but where the oil and water mixture inverted from water-continuous points 702 to oil-continuous at point 704. The methods of FIG. 1 or FIG. 4 can optionally include testing for whether the continuous phase behavior of the well or phase inversion behavior was characteristic of the well.

EXAMPLE 4

Figure 8:
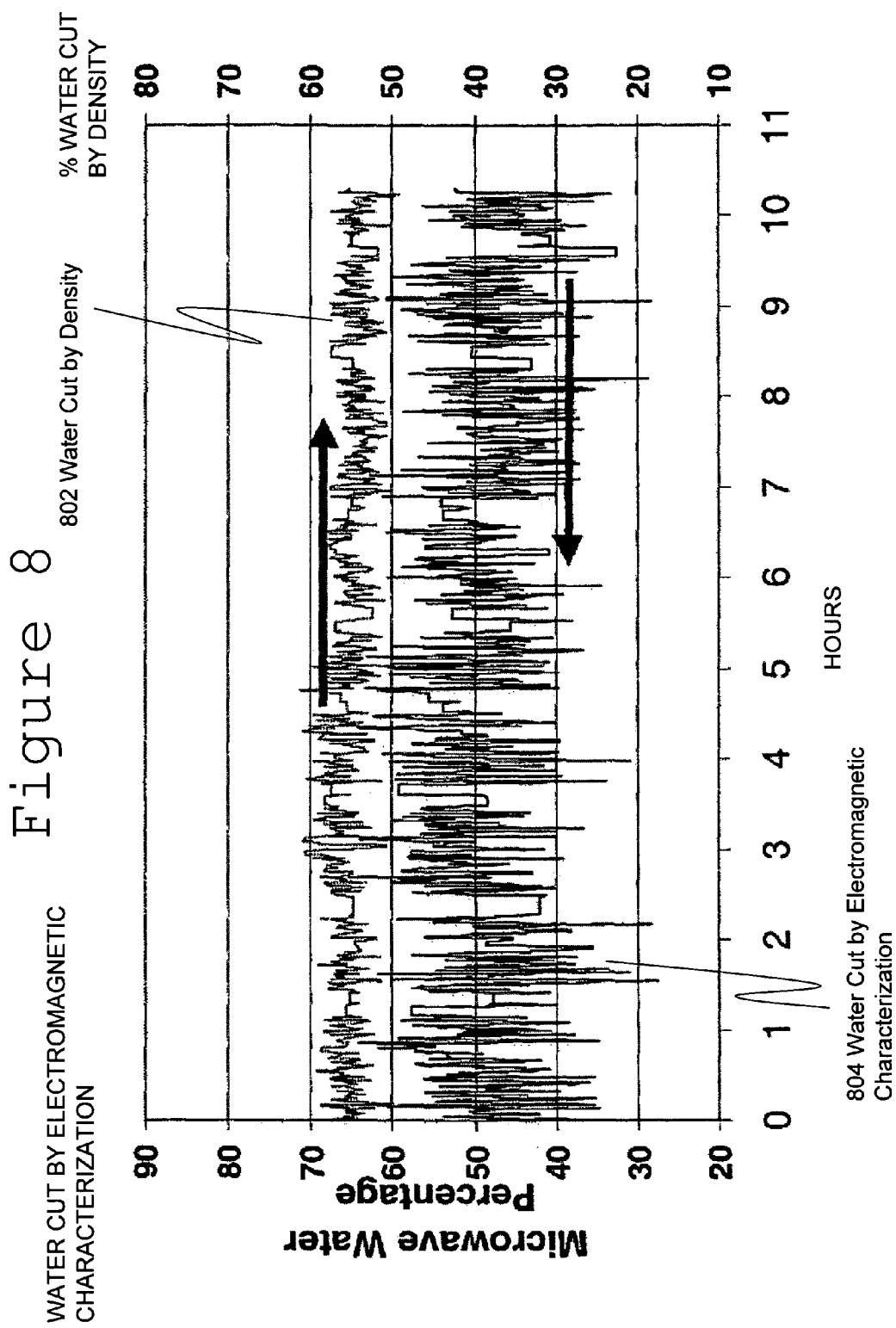
FIG. 8 shows actual water cut profile data for still another well over an 11 hour period, with both the water cut by density and water cut by electromagnetic characterization calculated and displayed, consistent with a preferred embodiment.

As another illustrative, non-limiting example, a preferred embodiment of the present invention can be applied to determine the water cut of a production well that experiences faults in the ability of the electrical characterization system 390 to properly choose the correct continuous phase. FIG. 8 shows actual data for a particular well for water cut by density 802 and water cut by electromagnetic characterization 804. It is obvious that the variance of water cut by density is less than the variance of water cut by electromagnetic characterization. In this case, if the assumption is made that the water cut by density lower variance indicates that the water cut by electromagnetic characterization is experiencing fault conditions, the methods of FIG. 1 and FIG. 4 can detect then exclude the fault condition, as shown in steps 416, 417, and 418.

According to a disclosed class of innovative embodiments, there is provided a method for characterizing fluid produced by a hydrocarbon well, comprising the actions of: (a) collecting a time series of data of property measurements of the fluid, (b) filtering said data to generate at least one time series subset, (c) assessing whether said subset provides acceptable data quality and providing at least one characterization measurement output if so, and (d) selectively adjusting at least one parameters for said filtering action, in dependence on said assessing action.

According to a disclosed class of innovative embodiments, there is provided a multiphase fluid characterization system, comprising a gas-liquid separator to separate a multiphase fluid into a gas stream and a liquid stream, a characterization stage which makes one or more property measurements of said liquid and said gas streams, and a logic circuit which collects a time series of measurements from said characterization stage, filters said time series to generate at least one time series subset, assesses whether said subset provides acceptable data quality and providing at least one characterization measurement output if so, and selectively adjusts at least one parameters for said filtering action, in dependence on said assessing action.

Modifications and Variations

As will be recognized by those skilled in the art, the innovative concepts described in the present application can be modified and varied over a range of applications, and accordingly the scope of patented subject matter is not limited by any of the specific exemplary teachings given. It is intended to embrace all such alternatives, modifications and variations that fall within the spirit and broad scope of the appended claims.

The methods and systems of the present application can operate across a wide range of processing situations and conditions. One of ordinary skill in the art, with the benefit of this disclosure, will recognize the appropriate use of the methods and systems for a chosen application of a given or dynamic set of operating parameters, including type of well, well pressure, well discharge temperature, discharge flow rate, multiphase fluid composition, aqueous phase composition, non-aqueous-phase composition, presence of condensible gases, presence of non-condensible gases, use of flow stream conditioning operations prior to characterization, flow stream pipe location, slip-stream installation versus full-stream installation versus insertion installation, characterization apparatus location, ambient temperature, or other conditions.

Optionally, the methods and systems of the present application can be configured or combined in various schemes. The combination or configuration depends partially on the required measuring precision and accuracy and the operational envelope of the process. One of ordinary skill in the art, with the benefit of this disclosure, will recognize the appropriate combination or configuration for a chosen application.

Optionally, the methods and systems of the present application can be used at the wellhead of (or slightly downstream from) a producing hydrocarbon well to improve the characterization of that well using at least some of the filtering parameters from another well sourcing hydrocarbon from the same reservoir, field, or subterranean formation as the well being tested. In this instance linkages 399 can used to communicate the filtering parameters inter-well.

Optionally, the methods and systems of the present application can be used at the wellhead of (or slightly downstream from) a producing hydrocarbon well to selectively adjust filtering parameters no more frequently than about once every two or three liquid phase hold-up periods for a particular well.

Optionally, multiphase fluid temperature compensation can be employed used to adjust for shifts in temperature using reference data sets relating temperature change to total fluid density change, or curves fitted to such reference data.

Optionally, because the thermal expansion of an oil continuous dispersion is generally different than the thermal expansion of a water-continuous dispersion, different reference data sets or curves fitted to such data sets may be employed.

Optionally, because the coefficient of thermal expansion for aqueous solutions and non-aqueous solutions differ, calculation routines can use the measured first phase fraction to better adjust for such temperature shifts. One of ordinary skill in the art, with the benefit of this disclosure, will recognize the appropriate systems to employ for such temperature compensation methods.

Optionally, methods such as the methods of FIG. 1 or FIG. 4 could include a subroutine incorporating the disclosure or teaching of Scott '613 to account for uncertainties in oil-continuous dispersions of less than about 5% water-cut.

Optionally, methods such as the methods of FIG. 1 or FIG. 4 could include a subroutine incorporating the disclosure or teaching of Scott '613 to adjust for shifts in the actual dry oil density away from the calibration dry oil density.

Optionally, examples of suitable hardware which can be fully or partially modified to fully or partially embody the methods and systems of the present application include those that are commercially available from Phase Dynamics of Richardson, Texas, under the name known to the industry as Compact Cyclone Multiphase Meter ("CCM").

Optionally, the systems of the present application may not include an on-board gas-liquid separator such as is present in the CCM, but where gases are essentially removed in a production separator, prior to conducting said time series of measurements.

Optionally, the systems of the present application may not include a densitometer such as is present in the CCM.

Optionally, the systems of the present application may not be located in a pipe or conduit. In one class of embodiments, the physical property measuring component and the electrical property measuring component may be located via an insertion installation in a vessel such as a storage tank, mixing tank, accumulator, separator, liquid-liquid contactor, or other processing device for which a multiphase fluid characterization is required. One of ordinary skill in the art, with the benefit of this disclosure, will recognize the appropriateness of the methods and systems of the present application for a chosen application.

Optionally, the systems of the present application can include a sampling port for comparison of the on-line determinations of first phase with an off-line determination.

Optionally, the pre-determined filtering parameters of the methods of the present application may not only be predetermined values of particular measurements or calculations to trigger filtering, but the parameters may be a sub-routine of equations, comparisons, noise reduction, or other data manipulation techniques. One of ordinary skill in the art of data manipulation, with the benefit of this disclosure, will recognize the appropriateness of such sub-routine options.

Optionally, the methods of the present application can also be embodied in a set of instructions that can be used on a general purpose desktop or laptop computer or microprocessor system, such as external system 374. The set of instructions can comprise input instructions that receives data from flow computer or microprocessor system 372. Similarly, the input instructions can accept instructions from a user via one or more input devices, such as a keyboard, mouse, touchpad, or other input device. The instructions can also implement the methods of the present invention or any part thereof to generate, for example, an updated transform for the calculation of first phase fraction by either the density method or the electromagnetic characterization method. The instructions can cause the computer or microprocessor system to display information, such as the results of the methods of the present invention, to a user, through a display monitor, printer, generated electronic file, or other such device. The instructions can also cause the computer or microprocessor system to transmit the results to a distant user via modem, cable, satellite, cell link, or other such means. For such digital communications, RS-422 or RS-485 can optionally be used to allow links from flow computer or microprocessor system 372 or external system 374 to multiple external units.

Optionally, a 4-20 milliamp analog output signal can be used to allow external processing of the system measurements.

Optionally, the methods of the present invention can also be embodied in a computer readable medium.

The present application frequently refers to "microwave" measurements for electromagnetic characterization which uses a baseline oscillator frequency in the VHF or UHF range. However, this term is used merely for convenience, and a variety of frequencies and methods can be used for electromagnetic characterization.

The preferred embodiment uses frequency measurement of a load-pulled oscillator to achieve electromagnetic characterization of a fluid flow which has some electromagnetic coupling to the oscillator's feedback path. This embodiment is particularly preferable, due to the sensitivity and rapid response of load-pulled measurement systems. However, it should be noted that many of the disclosed inventions can also (alternatively and less preferably) be applied to many other kinds of electromagnetic characterization systems.

Additional general background, which helps to show variations and implementations, may be found in the following publications, all of which are hereby incorporated by reference: Bentley N. Scott, Larry Baker, and Dr. Bjornar Svingen, 16$^{th}$ North Sea Flow Measurement Workshop 1998, "Well Testing Issues and a New Compact Cyclone System;" Compact Cyclone Multiphase Meter (CCM) Specifications Sheet, CCM Literature 0205, available on the Web at http://www.phasedynamics.com, (as of the filing date of this application); "Family of Water Cut Analyzers, Analyzer Family 0306," available on the Web at http://www.phasedynamics.com (as of the filing date of this application); and Babak Ghaempanah, Parviz Mehdizadeh, and Stuart L. Scott, "Improving the Quality of Production Data and Its Effect on Allocation Factor and Reserve Estimation," Society of Petroleum Engineers publication SPE 103319, 2006.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A method for characterizing a multiphase fluid produced by a hydrocarbon well, comprising the actions of:

storing a time series of electromagnetic characterization measurements and non-electrical characterization measurements taken on a liquid stream of the multiphase fluid in a memory;

filtering, by a characterization system, the electromagnetic characterization measurements and the non-electrical characterization measurements to remove measurements that are uncharacteristic of the hydrocarbon well during steady state operation;

calculating, by the characterization system, a first water percentage of the liquid stream for each time in the time series based on the filtered electromagnetic characterization measurements;

calculating, by the characterization system, a second water percentage of the liquid stream for each time in the time series based on the filtered non-electrical characterization measurements; and assessing, by the characterization system, an agreement between the first water percentage and the second water percentage for each time in the filtered time series to determine an overall data quality of the filtered electromagnetic characterization measurements and non-electrical characterization measurements.

2. The method of claim 1 further comprising:

if the overall data quality is at or above a threshold quality, outputting, by the characterization system, at least one characterization output pertaining to the hydrocarbon well; and if the overall data quality is below the threshold quality, recalculating, by the characterization system, the first water percentage and the second water percentage using additional electromagnetic characterization measurements and non-electrical characterization measurements taken on the liquid stream.

3. The method of claim 1, wherein the measurements that are uncharacteristic of the hydrocarbon well comprises measurements that are above a maximum value or below a minimum value.

4. The method of claim 1, wherein the measurements that are uncharacteristic of the hydrocarbon well comprises measurements that are taken during a start-up of the hydrocarbon well.

5. The method of claim 2, wherein the at least one characterization output is an average selected from the group consisting of water percentage, oil percentage, and gas percentage of the hydrocarbon well.

6. The method of claim 3, wherein the measurements that are uncharacteristic of the hydrocarbon well comprises measurements that are outside the liquid level constraints of a gas-liquid separator of the characterization system.

7. The method of claim 3, wherein the characterization system adjusts the maximum value and the minimum value based at least partly on the overall data quality.

8. A system for characterizing a multiphase fluid produced by a hydrocarbon well, comprising:

a memory for storing a time series of electromagnetic characterization measurements and non-electrical characterization measurements taken on a liquid stream of the multiphase fluid; and a processor for:

filtering the electromagnetic characterization measurements and the non-electrical characterization measurements to remove measurements that are uncharacteristic of the hydrocarbon well during steady state operation, calculating a first water percentage of the liquid stream for each time in the time series based on the filtered electromagnetic characterization measurements, calculating a second water percentage of the liquid stream for each time in the time series based on the filtered non-electrical characterization measurements, and assessing an agreement between the first water percentage and the second water percentage for each time in the filtered time series to determine an overall data quality of the filtered electromagnetic characterization measurements and non-electrical characterization measurements.

9. The system of claim 8, wherein if the overall data quality is at or above a threshold quality, the processor outputs at least one characterization output pertaining to the hydrocarbon well, and if the overall data quality is below the threshold quality, the processor recalculates the first water percentage and the second water percentage using additional electromagnetic characterization measurements and non-electrical characterization measurements taken on the liquid stream.

10. The system of claim 8, wherein the measurements that are uncharacteristic of the hydrocarbon well comprises measurements that are above a maximum value or below a minimum value.

11. The system of claim 8, wherein the measurements that are uncharacteristic of the hydrocarbon well comprises measurements that are taken during a start-up of the hydrocarbon well.

12. The system of claim 9, wherein the at least one characterization output is an average selected from the group consisting of water percentage, oil percentage, and gas percentage of the hydrocarbon well.

13. The system of claim 10, wherein the measurements that are uncharacteristic of the hydrocarbon well comprises measurements that are outside the liquid level constraints of a gas-liquid separator of the characterization system.

14. The system of claim 10, wherein the characterization system adjusts the maximum value and the minimum value based at least partly on the overall data quality.

* * * * *